United States Patent
Hu et al.

(10) Patent No.: US 10,988,456 B2
(45) Date of Patent: Apr. 27, 2021

(54) O-AMINOHETEROARYL ALKYNYL-CONTAINING COMPOUND, PREPARATION METHOD THEREFOR, AND USE THEREOF

(71) Applicant: SHANGHAI INSTITUTE OF MATERIA MEDICA, CHINESE ACADEMY OF SCIENCES, Shanghai (CN)

(72) Inventors: Youhong Hu, Shanghai (CN); Meiyu Geng, Shanghai (CN); Wenming Ren, Shanghai (CN); Jian Ding, Shanghai (CN); Xiaocong Guan, Shanghai (CN); Jing Ai, Shanghai (CN); Lang Wang, Shanghai (CN); Xia Peng, Shanghai (CN); Yang Liu, Shanghai (CN); Yang Dai, Shanghai (CN); Limin Zeng, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/487,385

(22) PCT Filed: Feb. 12, 2018

(86) PCT No.: PCT/CN2018/076423
§ 371 (c)(1),
(2) Date: Aug. 20, 2019

(87) PCT Pub. No.: WO2018/149382
PCT Pub. Date: Aug. 23, 2018

(65) Prior Publication Data
US 2020/0055838 A1 Feb. 20, 2020

(30) Foreign Application Priority Data
Feb. 20, 2017 (CN) .......................... 201710090242.8

(51) Int. Cl.
C07D 401/12 (2006.01)
C07D 405/14 (2006.01)
C07D 403/12 (2006.01)
A61P 35/00 (2006.01)
B01J 31/24 (2006.01)
B01J 27/122 (2006.01)
B01J 31/30 (2006.01)

(52) U.S. Cl.
CPC ............ C07D 401/12 (2013.01); A61P 35/00 (2018.01); B01J 27/122 (2013.01); B01J 31/2409 (2013.01); B01J 31/30 (2013.01); C07D 403/12 (2013.01); C07D 405/14 (2013.01); *B01J 2231/44* (2013.01); *B01J 2531/007* (2013.01); *B01J 2531/824* (2013.01)

(58) Field of Classification Search
CPC .. C07D 401/12; C07D 403/12; C07D 405/14; A61P 35/00; B01J 27/122; B01J 31/2409; B01J 31/30; B01J 2231/44; B01J 2531/007; B01J 2531/824
USPC ..................................................... 514/252.11
See application file for complete search history.

(56) References Cited

U.S. PATENT DOCUMENTS

2012/0196902 A1 8/2012 Boral et al.
2016/0102081 A1 4/2016 Boral et al.

FOREIGN PATENT DOCUMENTS

| CN | 101389338 A | 3/2009 |
| CN | 101490053 A | 7/2009 |
| CN | 103998431 A | 8/2014 |

(Continued)

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda
(74) *Attorney, Agent, or Firm* — Novick, Kim & Lee, PLLC; Bin Lu; Zhi Yang Xue

(57) ABSTRACT

An o-aminoheteroaryl alkynyl-containing compound has a structure represented by formula (I), and the compound of formula (I) has advantages of a high FGFR and RET double target inhibitory activity and a relatively low KDR activity, and the compound of formula (I) exhibits a strong inhibitory activity in a human lung cancer cell line NCI-H1581 and a gastric cancer cell line SNU16 as well as an RET-dependent sensitive cell line BaF3-CCDC6-Ret and a mutant thereof. Pharmacokinetic data shows that the o-aminoheteroaryl alkynyl-containing compound has druggability, and exhibits significant relevant inhibition of the growth of related tumors in a long-term animal model of drug efficacy and results in favorable animal condition at effective doses.

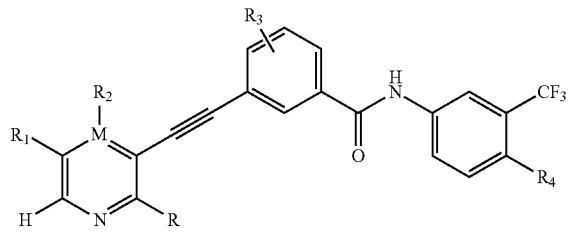

17 Claims, 2 Drawing Sheets

(56) References Cited

FOREIGN PATENT DOCUMENTS

| CN | 104211639 A | 12/2014 |
|---|---|---|
| CN | 104870446 A | 8/2015 |
| WO | 2006044823 A2 | 4/2006 |
| WO | 2013062843 A1 | 5/2013 |
| WO | 2015089210 A1 | 6/2015 |
| WO | 2015089220 A1 | 6/2015 |
| WO | 2015108490 A2 | 7/2015 |
| WO | 2016029776 A1 | 3/2016 |

OTHER PUBLICATIONS

Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Liu, Yang et al. "Discovery of novel Ponatinib analogues for reducing KDR activity as potent FGFRs inhibitors", European Journal of Medicinal Chemistry, vol. 126, Oct. 4, 2016 (Oct. 4, 2016), pp. 122-132, XP029885668, ISSN: 0223-5234.
Moccia, Marialuisa et al. "Identification of novel small molecule inhibitors of oncogenic RET kinase", PLoS One, vol. 10, No. 6, Jun. 5, 2015 (Jun. 5, 2015), pp. e0128364, XP055536588, ISSN: 1932-6203.
Deng, Xianming et al. "Broad spectrum alkynyl inhibitors of T315I Bcr-Abl", Bioorganic & Medicinal Chemistry Letters, vol. 20, No. 14, May 19, 2010 (May 19, 2010), pp. 4196-4200, Elsevier, XP027104017, ISSN: 0960-894X.
Thomas, Mathew et al. "Discovery of 5-(arenethynyl) hetero-monocyclic derivatives as potent inhibitors of BCR-ABL including the T315I gatekeeper mutant", Bioorganic & Medicinal Chemistry Letters, vol. 21, No. 12, Apr. 22, 2011 (Apr. 22, 2011), pp. 3743-3748, Elsevier, XP028091103, ISSN: 0960-894X.
Nicholas Turner et al. "Fibroblast growth factor signalling: from development to cancer", Nature Reviews Cancer. (2010), vol. 10:116-129, Macmillian Publishers Limited.
Dieci, Maria et al. "Fibroblast Growth Factor Receptor Inhibitors as a Cancer Treatment: From a Biologic Rationale to Medical Perspectives", Cancer Discovery. (2013) vol. 3, p. 264-279, American Association fro Cancer Research. DOI:10.1158/2159-8290.CD-12-0362.
Weiss, Jonathan et al. "Frequent and Focal FGFR1 Amplification Associates with Therapeutically Tractable FGFR1 Dependency in Squamous Cell Lung Cancer" Sci Transl Med., 2010, vol. 3, p. 1-18, NIH.
Amit Dutt et al.Inhibitor-Sensitive FGFR1 Amplification in Human Non-Small Cell Lung Cancer, PLoS One, 2011, Vo. 6, p. 1-10, e20351.
Matsumoto, K et al "FGFR2 gene amplification and clinicopathological features in gastric cancer." Br. J. Cancer, 2012, 106, 727-732, Cancer Research UK, doi:10.1038/bjc.2011.603.
Cheng, Ann-Lii et al. "Targeting Fibroblast Growth Factor Receptor Signaling in Hepatocellular Carcinoma", Oncology, 2011, vol. 81, p. 372-80, Karger, DOI: 10.1159/000335472.
Maria Borrello et al., "Induction of a proinflammolatory program in normal human thyrocytes by the RET/PTC1 oncogene", PNAS, Oct. 11, 2005, vol. 102, p. 14825-14830.
Lois M. Mulligan, "RET revisited: expanding the oncogenic portfolio", Nature Reviews Cancer, 2014, vol. 14, p. 173-186, Macmillan Publishers Limited.

* cited by examiner

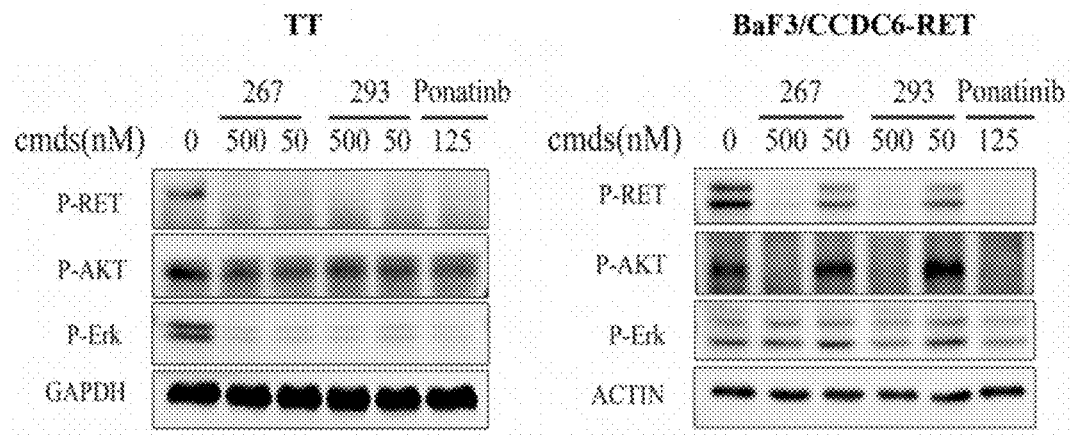
FIG. 1
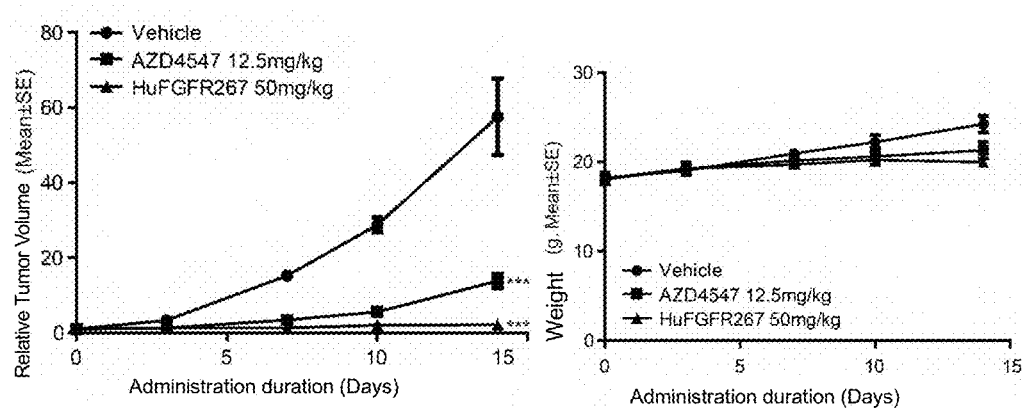
FIG. 2
FIG. 3

O-AMINOHETEROARYL ALKYNYL-CONTAINING COMPOUND, PREPARATION METHOD THEREFOR, AND USE THEREOF

FIELD OF THE INVENTION

The present invention relates to o-aminoheteroarylalkynyl-containing compound, preparation method therefor and use thereof.

BACKGROUND OF THE INVENTION

Receptor Tyrosine Kinase (RTK) is a class of transmembrane enzyme-linked receptor whose overexpression or overactivation is closely associated with the occurrence and development of tumors. Fibroblast Growth Factor Receptors (FGFRs) and the RET protein encoded by oncogene RET (Rearranged during Transfection) are important members of the RTK superfamily and important targets for tumor therapy.

FGFRs mainly include four subtypes, FGFR1, FGFR2, FGFR3 and FGFR4 (Turner N., Grose R., Fibroblast growth factor signalling: From development to cancer, Nature Reviews Cancer. (2010) 10:116-129; Dieci M. V., Arnedos M., Andre F., Soria J. C., Fibroblast Growth Factor Receptor Inhibitors as a Cancer Treatment: From a Biologic Rationale to Medical Perspectives, Cancer Discovery. (2013) 3:264-279.) Overexpression or overactivation of FGFRs by means of gene amplification, mutation, fusion or ligand induction, plays an important role in promoting tumor cell proliferation, invasion, migration and tumor angiogenesis. It is found in the study that FGFRs are overexpressed or overactivated in various tumors such as non-small cell lung cancer, breast cancer, stomach cancer, bladder cancer, endometrial cancer, prostate cancer, cervical cancer, colon cancer, esophageal cancer, keratinoma, myeloma, rhabdomyosarcoma, etc. (Dieci M V, Arnedos M, Andre F, Soria J C: Fibroblast growth factor receptor inhibitors as a cancer treatment: From a biologic rationale to medical perspectives. *Cancer discovery*, 2013, 3, 264-79; Turner N, Grose R: Fibroblast growth factor signalling: From development to cancer. *Nat. Rev. Cancer*, 2010, 10, 116-29.) For example, overactivation of FGFR1 signaling pathway in squamous cell carcinoma of non-small cell lung cancer is up to 20%; (Frequent and Focal FGFR1 Amplification Associates with Therapeutically Tractable FGFR1 Dependency in Squamous Cell Lung Cancer (vol 3, 66er5, 2011), Sci Transl Med. (2010); Inhibitor-Sensitive FGFR1 Amplification in Human Non-Small Cell Lung Cancer, PLoS ONE. (2011) 6:e20351) The overactivation of FGFR2 signaling pathway in gastric cancer accounts for 5-10% (Matsumoto K, Arao T, Hamaguchi T, Shimada Y, Kato K, Oda I, Taniguchi H, Koizumi F, Yanagihara K, Sasaki H, Nishio K, Yamada Y: FGFR2 gene amplification and clinicopathological features in gastric cancer. *Br. J. Cancer*, 2012, 106, 727-32). FGFR3 mutation in bladder cancer accounts for 50%-60% (non-invasive) and 10%-15% (invasive). Various subtypes of FGFR are overexpressed and overactivated in liver cancer, such as FGFR2, FGFR3, FGFR4, etc. (Cheng A L, Shen Y C, Zhu A X: Targeting Fibroblast Growth Factor Receptor Signaling in Hepatocellular Carcinoma. *Oncology-Basel*, 2011, 81, 372-80).

RET is also a member of RTK family and its normal physiological functions include renal development, development of the nervous system, maintenance and renewal of sperm stem cells, differentiation of myelomonocytic cells, formation of lymphoid tissues, etc. RET is expressed in human intestinal ganglion cells, neuroblastoma, pheochromocytoma, medullary thyroid carcinoma, thyroid C cells, and melanocytes, etc. In recent years, based on intensive study on RET, it has been found that overactivation of RET in tumors significantly promotes proliferation, survival, invasion, metastasis, and tumor inflammation of various tumors (Maria Grazia Borrello, Induction of a proinflammolatory program in normal human thyrocytes by the RET/PTC1 oncogene, PNAS, Oct. 11, 2005). For example, RET point mutation is up to 95% in patients with medullary thyroid carcinoma; RET gene rearrangement accounts for 20% to 40% in patients with papillary thyroid cancer; and RET is also overexpressed in adenocarcinoma, colon cancer, pancreatic cancer, breast cancer, acute leukemia. (Lois M. Mulligan: RET revisited: Expanding the oncogenic portfolio, Nature Reviews Cancer 14, 173-186 (2014)).

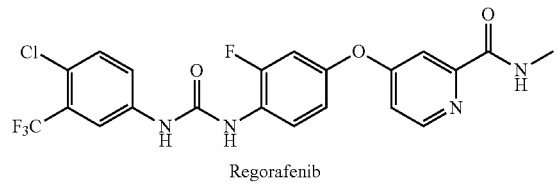 [SMILES: CNC(=O)c1cc(Oc2ccc(NC(=O)Nc3ccc(Cl)c(C(F)(F)F)c3)c(F)c2)ccn1]

Regorafenib

Currently, the marketed drugs as a multi-targeted inhibitor having FGFR and RET inhibitory activity mainly target vascular endothelial growth factor receptor 2 (VEGFR2, also known as KDR), such as Regorafenib. Studies have shown that the strong inhibition of KDR causes cancer patients to have strong cardiovascular side effects, such as thrombotic microangiopathy, hypertension, congestive heart failure, coagulopathy, pancreatitis and so on. Based on current studies, there is few report on RET inhibitors with strong selectivity. Meanwhile, the inevitable drug resistance problem in other kinase inhibitors also exists in RET inhibitors. For example, the classic gatekeeper site mutations—RET V804M and V804L have been discovered. Currently, preclinical studies have shown that few inhibitors have the potential to overcome resistance.

The compounds disclosed in the Boral Sougato's patent must have sulfone imine (US2012196902A1, WO2013062843A1, WO2015089210A1, WO2015089220A1) or tetrazolium (US2016102081A1) as advantageous structure at meta-position of the pyridine ring, and focus on VEGFR. The compounds have low druggability, low exposure in vivo, and fail to achieve anti-tumor effect in vivo.

Kassoum Nacro's patent discloses a series of amino-substituted nitrogen-containing heteroaromatic ring (WO2015108490A2) whose target is tyrosine kinase MNK. However, as for A ring, it doesn't specifically disclose o-amino substituted heterocycle.

CN201310224333.8 disclosed a class of alkynyl heterocyclic compounds and uses thereof. However, o-amino substituted heteroaryl ring is not disclosed either.

SUMMARY OF THE INVENTION

The present invention provides a novel o-aminoheteroaryl alkynyl-containing compound, preparation method therefor and use thereof.

The present invention is implemented by the following technical solutions:

A compound of formula (I), or a deuterated compound, or a pharmaceutically acceptable salt or a prodrug thereof:

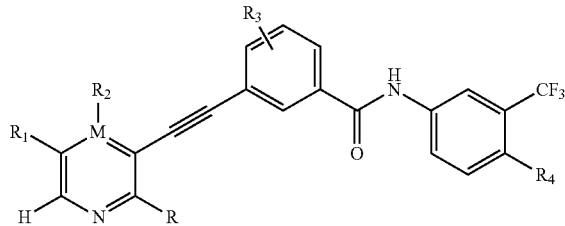

wherein:
R is amino which is optionally substituted by one or more alkyl or modified alkyl;
M is C or N, and when M is N, $R_2$ is none;
$R_1$ is selected from —H, —N($Q_1$)($Q_2$), amino, halogen, hydroxyl, cyano, aryl, heteroaryl, alkyl or modified alkyl;
$R_2$ is selected from —H, —N($Q_1$)($Q_2$), amino, halogen, hydroxyl, oxo, aryl, heteroaryl, alkyl or modified alkyl;
$R_3$ is selected from —H, halogen, cyano, alkyl or modified alkyl;
$R_4$ is selected from —(CH$_2$)$_n$N($R_7$)($R_8$), —NHR$_9$, —OR$_9$ or modified alkyl;
$R_7$, and $R_8$ together with the adjacent N atom form a heteroaryl ring;
$R_9$ is selected from —H, aryl or heteroaryl;
each of $Q_1$ and $Q_2$ is independently selected from —H, aryl, alkyl or modified alkyl, and at least one of $Q_1$ and $Q_2$ is an aryl;
each of the aryl, heteroaryl, heteroaryl ring is independently and optionally substituted by one or more substituents selected from the group consisting of halogen, oxo, alkyl and modified alkyl;
the alkyl is a saturated aliphatic straight or branched alkyl group having 1-6 carbon atoms;
the modified alkyl is an alkyl having 1-6 carbon atoms in which any carbon (primary, secondary, tertiary or quaternary carbon group) is substituted with one or more substituents selected from —O—, —OH, —(C═O)—, halogen, primary amino, secondary amino, tertiary amino, cycloalkyl, cycloalkylene, heterocyclyl, and heterocyclylene, and a carbon-carbon single bond of the alkyl are optionally and independently replaced by a carbon-carbon double bond or a carbon-carbon triple bond;
the halogen is each independently selected from the group consisting of F, Cl, Br, and I;
the aryl is a 5-10 membered monocyclic or fused bicyclic ring;
the heteroaryl or heteroaryl ring is a 5-10 membered aromatic monocyclic or fused bicyclic ring having one or more heteroatoms selected from N, O, and S;
the cycloalkyl is a saturated or unsaturated 3-10 membered monocyclic or polycyclic alicyclic ring;
the cycloalkylene is a saturated or unsaturated 3-10 membered monocyclic or polycyclic aliphatic cycloalkylene;
the heterocyclyl is a saturated or unsaturated 3-10 membered monocyclic or polycyclic aliphatic heterocycle containing one or more heteroatoms selected from N, O, and S;
the heterocyclylene is a saturated or unsaturated 3-10 membered monocyclic or polycyclic aliphatic heterocyclylene containing one or more heteroatoms selected from N, O, and S;
n is 0-3;
preferably, the pharmaceutically acceptable salt comprises hydrochloride, methanesulfonate, maleate or the like, and the prodrug comprises ester, amide, carboxamide or the like of the formula (I) compound.

Preferably, in the above compound of formula (I) or the deuterated compound, or pharmaceutically acceptable salt or prodrug thereof,
the alkyl is a saturated aliphatic straight or branched alkyl having 1-6 carbon atoms, preferably having 1-4 carbon atoms, more preferably 1-3 carbon atoms, and still more preferably is methyl, ethyl, propyl, isopropyl or tert-butyl;
the modified alkyl is an alkyl having one or more substituents selected from the group consisting of —O—, —COO—, —CONH—, —CH═CH—, —C≡C—, halogen, hydroxyl, carboxyl, primary amino, secondary amino, tertiary amino, cycloalkyl, heterocyclyl, and heterocyclylene;
the aryl is a 6-10 membered and preferably 6-8 membered monocyclic or fused bicyclic ring;
the heteroaryl or heteroaryl ring is a 6-10 membered and preferably 6-8 membered monocyclic or fused bicyclic ring containing 1-3 heteroatoms selected from N, O and S;
the cycloalkyl is a saturated or unsaturated 3-6 membered monocyclic or polycyclic ring;
the cycloalkylene is a saturated or unsaturated 3-6 membered monocyclic or polycyclic ring;
the heterocyclyl is a 4-7 membered and preferably 4-6 membered monocyclic or polycyclic heterocycle containing 1-3 heteroatoms selected from N, O, and S;
the heterocyclylene is a 4-7 membered and preferably 4-6 membered monocyclic or polycyclic heterocycle containing 1-3 heteroatoms selected from N, O, and S;
n is 0 to 1.

Preferably, in the above compound of formula (I) or deuterated compound, or pharmaceutically acceptable salt or prodrug thereof:
R is amino;
M is C or N, and when M is N, $R_2$ is none;
$R_1$ is selected from: —H, —N($Q_1$)($Q_2$), —N($Q_1$')($Q_2$'), halogen, hydroxyl, cyano, $C_1$-$C_6$ alkyl (optionally substituted by 1 to 5 halogens), amino $C_1$-$C_6$ alkyl, methylamino $C_1$-$C_6$ alkyl, dimethylamino $C_1$-$C_6$ alkyl, $C_1$-$C_6$ alkoxyl, hydroxyl $C_1$-$C_6$ alkyl, $C_3$-$C_6$ cycloalkyl, carboxyl, —C(═O)O($C_1$-$C_6$ alkyl), —C(═O)NH($C_1$-$C_6$ alkyl), $C_6$-$C_{10}$ aryl, 5-8 membered heteroaryl or 4-7 membered heterocyclyl;
$R_2$ is selected from —H, —N($Q_1$)($Q_2$), —N($Q_1$')($Q_2$'), halogen, hydroxyl, oxo, $C_1$-$C_6$ alkyl (optionally substituted by 1-5 halogens), amino $C_1$-$C_6$ alkyl, methylamino $C_1$-$C_6$ alkyl, dimethylamino $C_1$-$C_6$ alkyl, $C_1$-$C_6$ alkoxy, hydroxyl $C_1$-$C_6$ alkyl, $C_3$-$C_6$ cycloalkyl, $C_6$-$C_{10}$ aryl, 5-8 membered heteroaryl or 4-7 membered heterocyclyl;
each of $Q_1$ and $Q_2$ is independently selected from —H, $C_1$-$C_6$ alkyl, $C_3$-$C_6$ cycloalkyl, $C_1$-$C_6$ alkanoyl, $C_1$-$C_6$ enoyl or phenyl, and at least one of $Q_1$ or $Q_2$ is phenyl, wherein the phenyl is optionally substituted by one or more substituents selected from the group consisting of halogen, $C_1$-$C_6$ alkyl, $C_1$-$C_6$ haloalkyl, and $C_1$-$C_6$ alkoxyl;
each of $Q_1$' and $Q_2$' is independently selected from the group consisting of —H, $C_1$-$C_6$ alkyl, $C_3$-$C_6$ cycloalkyl, $C_1$-$C_6$ alkanoyl and $C_1$-$C_6$ enoyl;
$R_3$ is selected from —H, halogen, cyano, an optionally halogenated $C_1$-$C_6$ alkyl, $C_1$-$C_6$ alkoxy or $C_3$-$C_6$ cycloalkyl;

$R_4$ is selected from —(CH$_2$)nN(R$_7$')(R$_8$'), —NHR$_9$' or —OR$_9$';

wherein n is 0 or 1;

$R_7$' and $R_8$' are each independently selected from —H, an optionally halogenated $C_1$-$C_6$ alkyl, $C_3$-$C_6$ cycloalkyl; or $R_7$' and $R_8$' together with the adjacent N atom form a 5-10 membered heteroaryl ring or a 4-10 membered heterocycle;

$R_9$' is selected from $C_6$-$C_{10}$ aryl, 5-10 membered heteroaryl, or 4-7 membered heterocyclyl;

the $C_6$-$C_{10}$ aryl, 5-10 membered heteroaryl, 4-7 membered heterocyclyl, 5-10 membered heteroaryl ring, and 4-10 membered heterocycle are optionally and independently substituted by one or more substituents selected from the group consisting of halogen, oxo, $C_1$-$C_6$ alkyl, $C_1$-$C_6$ haloalkyl, and $C_1$-$C_6$ alkoxy;

each of the 5-10 membered heteroaryl, the 4-7 membered heterocyclyl, the 5-10 membered heteroaryl ring, and the 4-10 membered heterocycle independently contains 1-3 heteroatoms selected from N, O, and S;

preferably, the $C_6$-$C_{10}$ aryl is optionally substituted with 1-5 substituents selected from the group consisting of halogen, $C_1$-$C_6$ alkyl, $C_1$-$C_6$ haloalkyl, and $C_1$-$C_6$ alkoxyl.

Preferably, in the above compound of formula (I) or the deuterated compound, or pharmaceutically acceptable salt or prodrug thereof:

M is C or N, and when M is N, $R_2$ is none;

$R_1$ is selected from —H, —N(Q$_1$)(Q$_2$), —N(Q$_1$')(Q$_2$'), $C_1$-$C_4$ alkyl (optionally substituted with 1-3 halogens), amino $C_1$-$C_4$ alkyl, methylamino $C_1$-$C_4$ alkyl, dimethylamino $C_1$-$C_4$ alkyl, $C_1$-$C_4$ alkoxy, hydroxy $C_1$-$C_4$ alkyl, $C_3$-$C_6$ cycloalkyl, carboxyl, —C(=O)O($C_1$-$C_4$ alkyl), —C(=O)NH($C_1$-$C_4$ alkyl), $C_6$-$C_{10}$ aryl, 5-6 membered heteroaryl or 4-6 membered heterocyclyl;

$R_2$ is selected from —H, halogen, hydroxy, oxo, $C_1$-$C_4$ alkyl (optionally substituted with 1-3 halogens), amino $C_1$-$C_4$ alkyl, methylamino $C_1$-$C_4$ alkyl, dimethylamino $C_1$-$C_4$ alkyl, $C_1$-$C_4$ alkoxy, hydroxy $C_1$-$C_4$ alkyl, $C_3$-$C_6$ cycloalkyl, $C_6$-$C_{10}$ aryl, 5-6 membered heteroaryl or 4-6 membered heterocyclic;

each of Q$_1$ and Q$_2$ is each independently selected from —H, $C_1$-$C_4$ alkyl, $C_3$-$C_6$ cycloalkyl, $C_1$-$C_4$ alkanoyl, $C_1$-$C_4$ enoyl or phenyl, and at least one of Q$_1$ and Q$_2$ is phenyl, wherein the phenyl is optionally substituted with one or more substituents selected from the group consisting of halogen, $C_1$-$C_4$ alkyl, $C_1$-$C_4$ haloalkyl, and $C_1$-$C_4$ alkoxy;

each of Q$_1$' and Q$_2$' is independently selected from the group consisting of —H, $C_1$-$C_4$ alkyl, $C_3$-$C_6$ cycloalkyl, $C_1$-$C_4$ alkanoyl, and $C_1$-$C_4$ enoyl;

$R_3$ is selected from —H, halogen, an optionally halogenated $C_1$-$C_4$ alkyl, $C_1$-$C_4$ alkoxy, or $C_3$-$C_4$ cycloalkyl;

$R_4$ is selected from —OR$_9$', —CH$_2$N (R$_7$')(R$_8$');

$R_7$' and $R_8$' are each independently selected from —H, an optionally halogenated $C_1$-$C_6$ alkyl, or $C_3$-$C_6$ cycloalkyl; or $R_7$' and $R_8$' together with the adjacent N atom form a 5-10 membered heteroaryl ring or a 4-10 membered heterocycle;

$R_9$ is selected from $C_6$-$C_{10}$ aryl, 5-10 membered heteroaryl, or 4-7 membered heterocyclyl;

the $C_6$-$C_{10}$ aryl, 5-6 membered heteroaryl, and 4-6 membered heterocyclyl are each independently and optionally substituted with one or more substituents selected from the group consisting of halogen, $C_1$-$C_4$ alkyl, $C_1$-$C_4$ haloalkyl, and $C_1$-$C_4$ alkoxyl;

the 5-10 membered heteroaryl or heteroaryl ring, and 4-10 membered heterocycle are each independently and optionally substituted with one or more substituents selected from the group consisting of halogen, oxo, $C_1$-$C_6$ alkyl, $C_1$-$C_6$ haloalkyl, and $C_1$-$C_6$ alkoxyl;

each of the 5-6-membered heteroaryl, 4-6 membered heterocyclyl, 5-10 membered heteroaryl or heteroaryl ring, and 4-10 membered heterocycle independently contains 1-3 heteroatoms selected from N, O, and S;

preferably, the $C_6$-$C_{10}$ aryl is optionally substituted with 1-4 substituents selected from the group consisting of halogen, $C_1$-$C_6$ alkyl, $C_1$-$C_6$ haloalkyl, and $C_1$-$C_6$ alkoxyl.

Preferably, in the above compound of formula (I) or the deuterated compound thereof, or pharmaceutically acceptable salt or prodrug thereof, M is C or N, and when M is N, $R_2$ is none;

R is amino;

$R_1$ is selected from the group consisting of —H, halogen, hydroxyl, cyano, $C_{1-4}$ alkyl (optionally substituted by halogen, hydroxyl, $C_{1-4}$ alkoxy, trifluoromethoxyl, mono or di $C_{1-4}$ alkylamino), $C_{1-4}$ alkoxy (optionally substituted by halogen, hydroxyl, $C_{1-4}$ alkoxyl, amino, mono or di $C_{1-4}$ alkylamino), amino, mono or di $C_{1-4}$ alkylamino, $C_{1-4}$ alkylamido, $C_{3-6}$ cycloalkylamido, and $C_{2-4}$ alkenylamido optionally substituted by mono or di $C_{1-4}$ alkylamino; preferably, $R_1$ is selected from —H, halogen, hydroxyl, cyano, methyl, trifluoromethyl, methoxy, trifluoromethoxy, cyclopropyl, cyclopropyloxy, epoxybutyloxy,

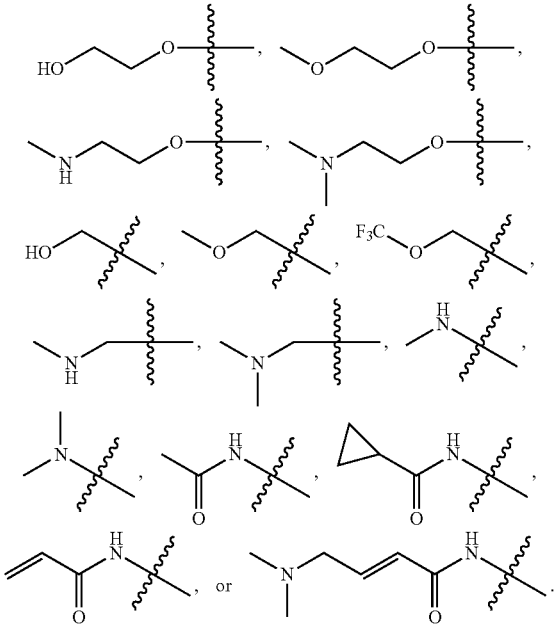

$R_2$ is selected from —H, or halogen;

$R_3$ is selected from the group consisting of —H, halogen, cyano, an optionally halogenated $C_{1-4}$ alkyl, and $C_{1-4}$ alkoxy; preferably $R_3$ is hydrogen, chloro, fluoro, methyl, methoxyl, cyano, or trifluoromethyl;

$R_4$ is a $C_{1-4}$ alkyl or oxyl substituted by a 5- or 6-membered aliphatic heterocyclyl having 1-2 N atoms on the ring, wherein the 5- or 6-membered aliphatic heterocyclyl is optionally substituted by $C_{1-4}$ alkyl, and preferably $R_4$ is 4-methylpiperazin-1-ylmethyl or 1-methylpiperidin-4-yloxyl.

Preferably, in the above compound of formula (I) or the deuterated compound, or pharmaceutically acceptable salt or prodrug thereof, the preferred compound, or the deuterated compound, or pharmaceutically acceptable salt or prodrug thereof is selected from the following compounds:

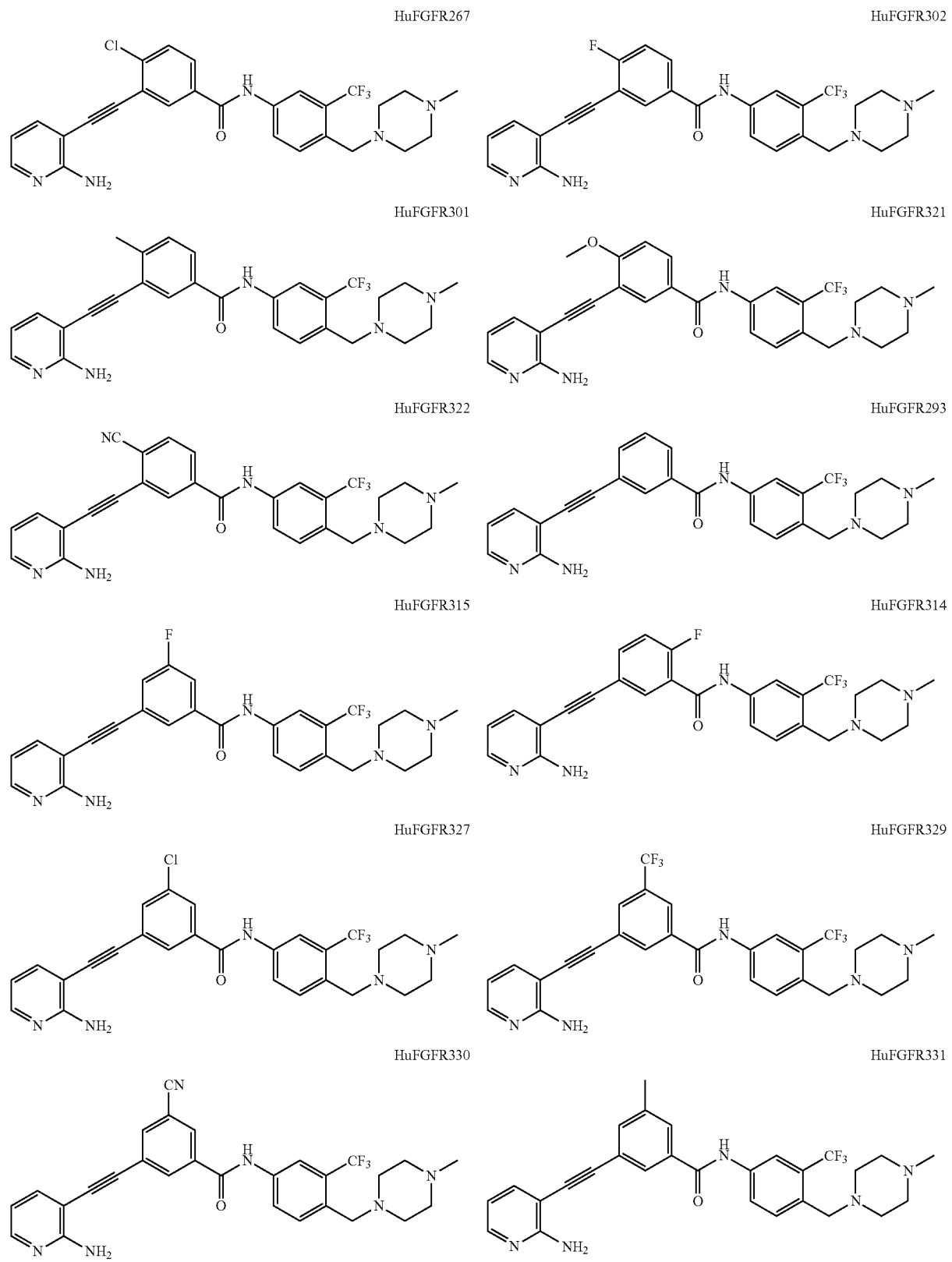

-continued
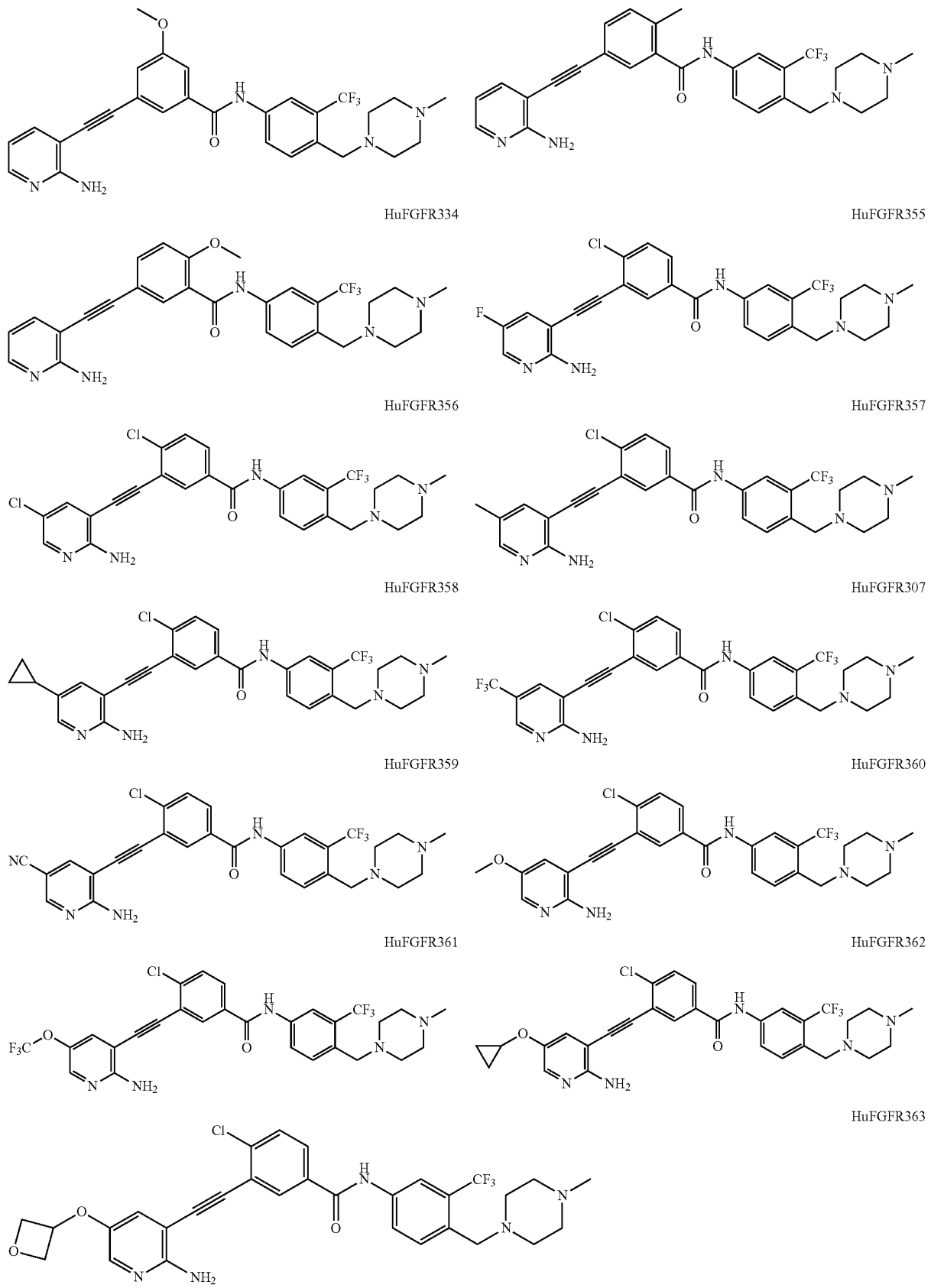

HuFGFR377
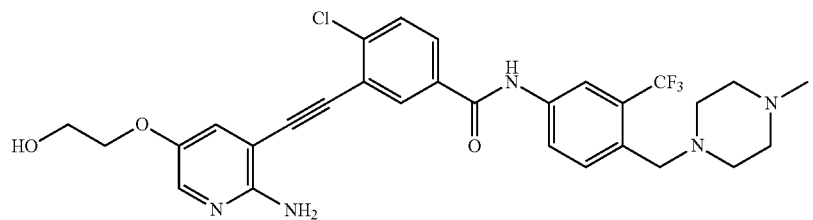
HuFGFR378
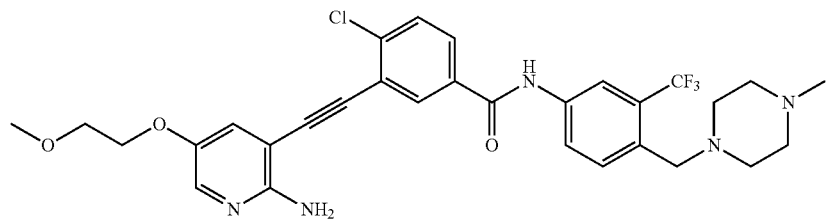
HuFGFR379
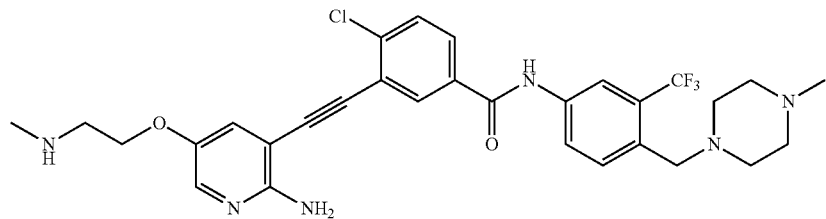
HuFGFR380
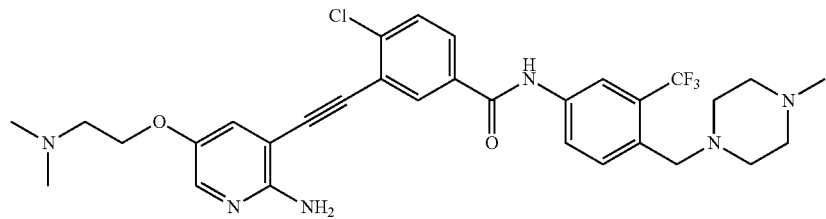
HuFGFR384
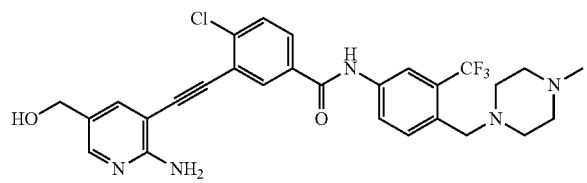
HuFGFR385
HuFGFR386
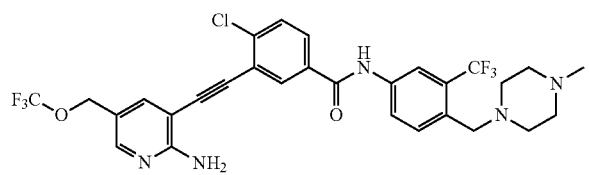
HuFGFR387
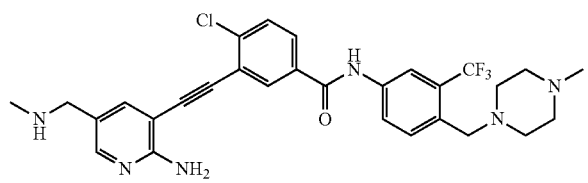
HuFGFR388
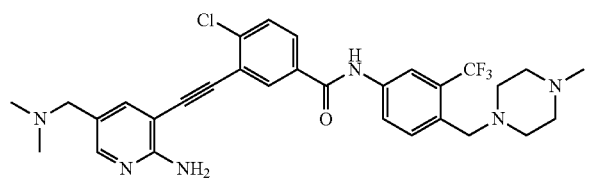
HuFGFR389
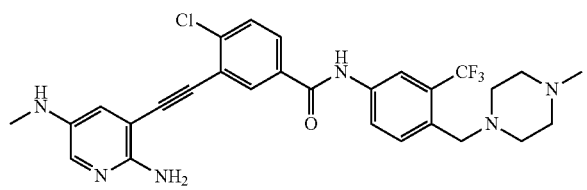

-continued
HuFGFR390
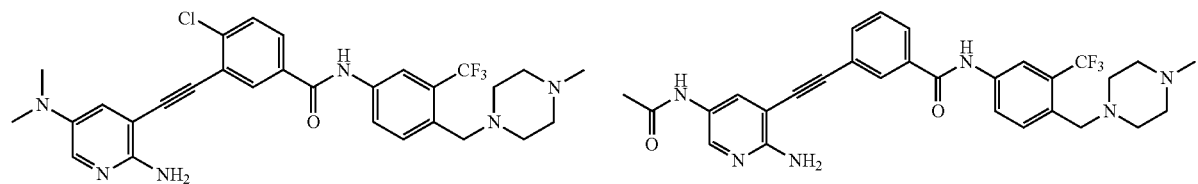
HuFGFR392
HuFGFR396
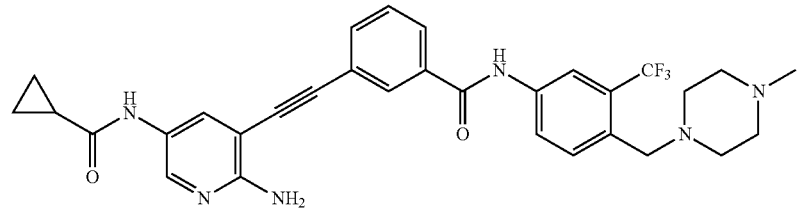
HuFGFR284
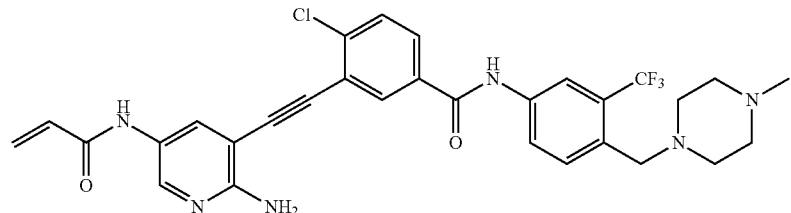
HuFGFR411
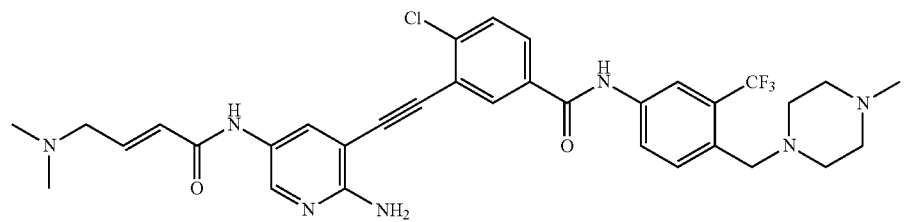
HuFGFR313
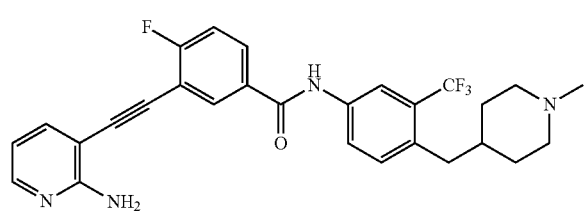
HuFGFR310
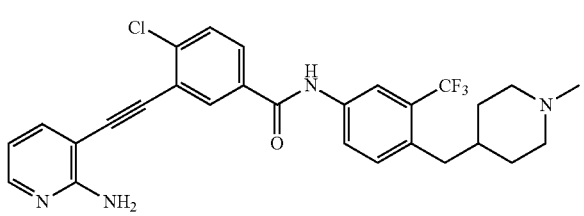
HuFGFR402
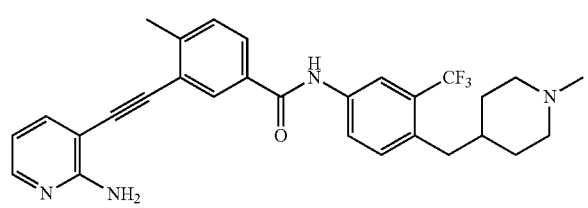
HuFGFR403
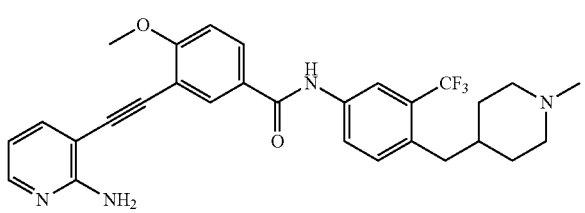
HuFGFR312
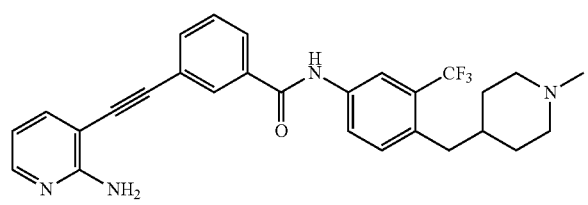
HuFGFR268
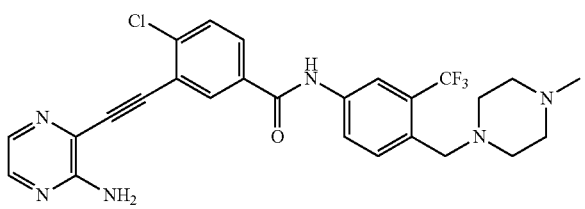

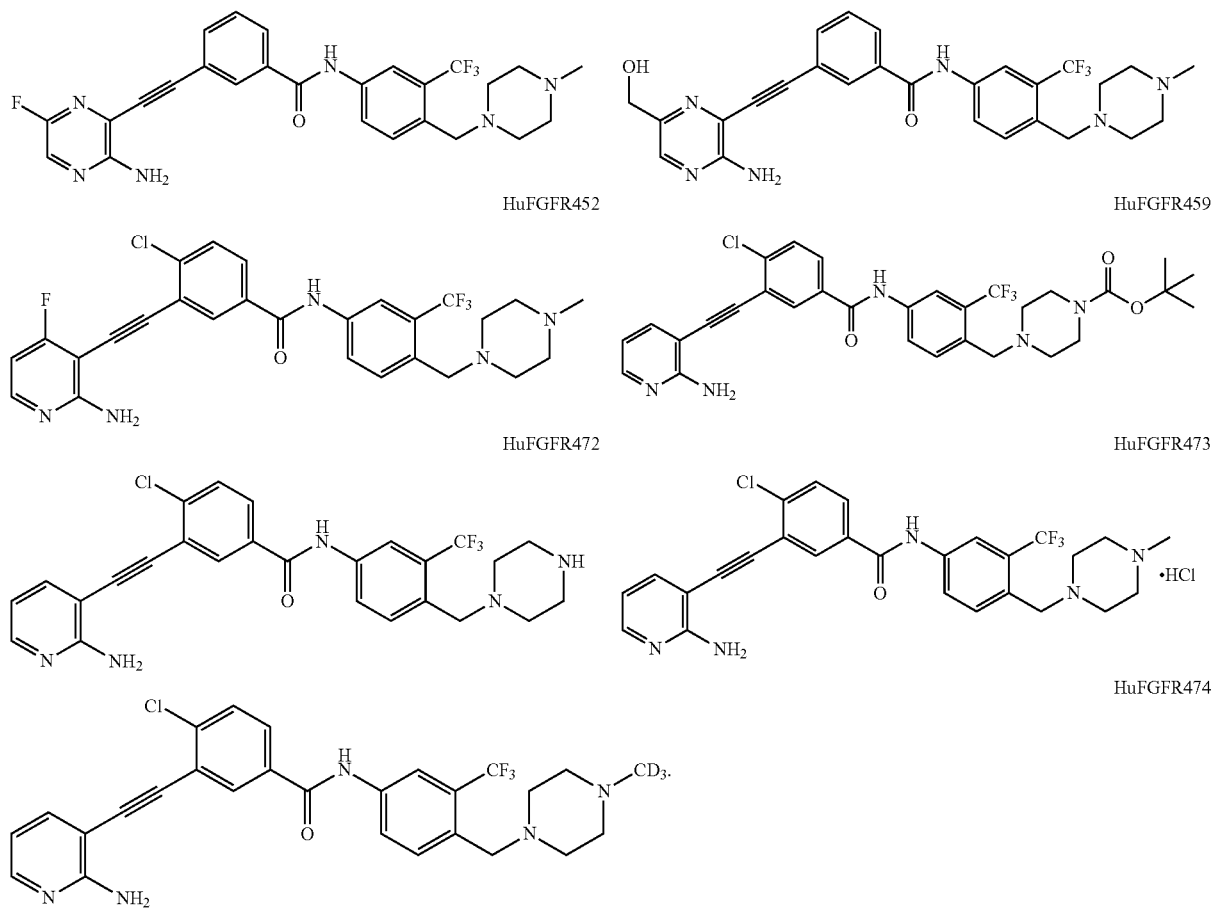

The present invention also provides a method for preparing the compound of formula (I), or the deuterated compound, or pharmaceutically acceptable salt or prodrug thereof, which comprises a step of reacting a compound of formula (1) with a compound of formula (2)

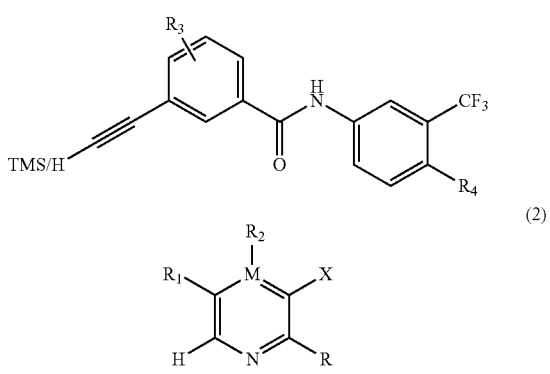

wherein, each of R and $R_1$-$R_4$ is independently defined as above.

Preferably, it comprises: in the presence of a transition metal palladium and copper catalyst and in alkaline condition, coupling the compound of formula (1) with the compound of formula (2). Preferably, the palladium catalyst comprises $Pd(PPh_3)_2Cl_2$, $Pd(OAc)_2$, and/or $Pd(PPh_3)_4$. Preferably, the copper catalyst comprises CuI and/or CuCl. Preferably, the base used for the alkaline condition comprises one or more bases selected from CsF, $Cs_2CO_3$, $K_2CO_3$, triethylamine, diisopropylethylamine, and DMAP. Preferably, the solvent for coupling reaction comprises one or more solvents selected from acetonitrile, 1,4-dioxane, and DMF.

More preferably, the method comprises a step of reacting the compound of formula (1) with the compound of formula (2) in the presence of cesium fluoride, $Pd(PPh_3)_2Cl_2$, CuI and triethylamine and in acetonitrile as a solvent.

More preferably, the method comprises any of the following Schemes I or II:

Scheme I

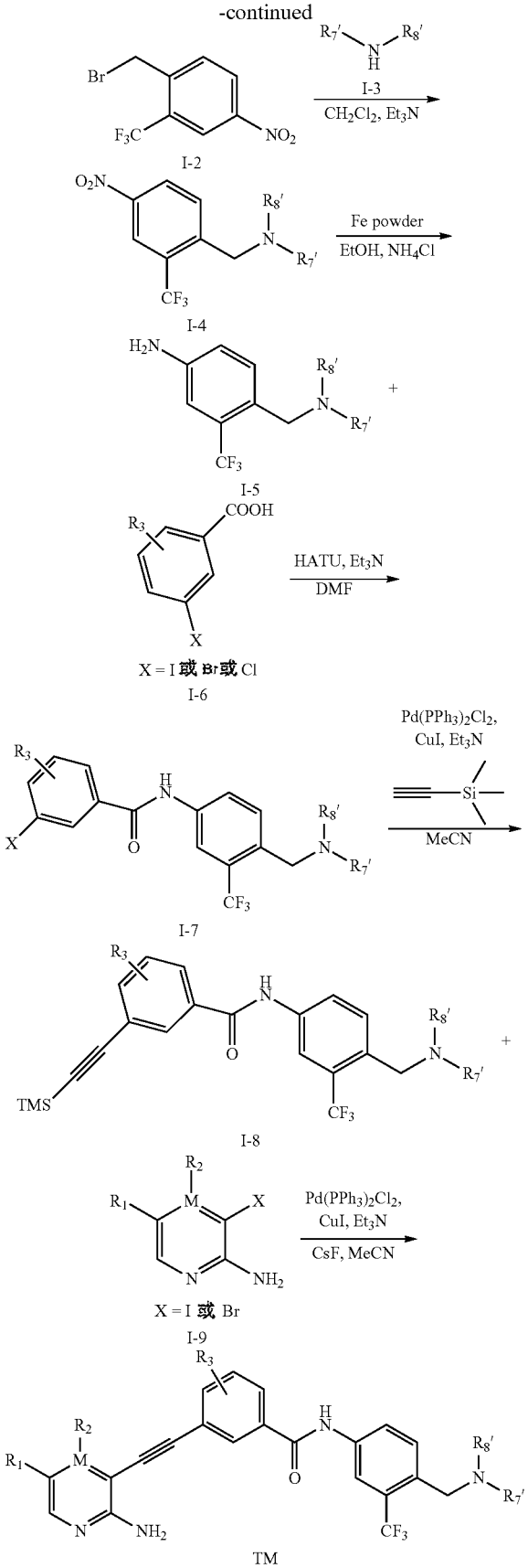

Scheme I includes the following steps:

Step 1: compound I-1, NBS, AIBN and CCl$_4$ are added into a round-bottom flask, and the reaction is carried out by heating in an oil bath under a reaction temperature of 100° C. for 24 hours until completion, and the compound I-2 is obtained by purification; wherein the equivalent ratio of compound I-1:NBS:AIBN is 1:1.1:0.2.

Step 2: compound I-2, I-3, CH$_2$Cl$_2$ and Et$_3$N are added into a round-bottom flask, and the reaction is carried out at room temperature for 12 hours until completion, and the compound I-4 is obtained by purification; wherein the equivalent ratio of the compound I-2:the compound I-3:Et$_3$N is 1:1.1:1.2.

Step 3: compound I-4, reducing agent (Fe powder), EtOH and NH$_4$Cl are added into a round-bottom flask, and the reaction is carried out by heating in an oil bath under a reaction temperature of 100° C. for 10 hours until completion, and the compound I-5 is obtained by purification; wherein the equivalent ratio of compound I-4:reducing Fe powder:NH$_4$Cl is 1:4:2.

Step 4: compound I-6, HATU, Et$_3$N, DMF are added into a round-bottom flask, and mixture is stirred at room temperature for 30 min, then compound I-5 is added, and stirring is continued at room temperature for 12 hours; after the reaction is completed, compound I-7 is obtained by purification; wherein the equivalent ratio of compound I-6:HATU:Et$_3$N:compound I- is 1:2:2:0.9.

Step 5: compound I-7, trimethylsilylacetylene, Pd(PPh$_3$)$_2$Cl$_2$, CuI and Et$_3$N are added into a round-bottom flask and MeCN is used as a solvent, and the mixture is heated to 80° C. in oil bath for 12 hours until reaction is completed, and the compound I-8 is obtained by purification; wherein the equivalent ratio of compound I-7:trimethylsilylacetylene:Pd(PPh$_3$)$_2$Cl$_2$:CuI:Et$_3$N is 1:1.5:0.05:0.1:3;

Step 6: compound I-8, compound I-9, cesium fluoride, Pd(PPh$_3$)$_2$Cl$_2$, CuI and Et$_3$N are added into a round-bottom flask and MeCN is used as a solvent, and the mixture is heated to 80° C. in oil bath for 12 hours until reaction is completed, and the compound TM is obtained by purification; wherein the equivalent ratio of compound I-8:compound I-9:cesium fluoride:Pd(PPh$_3$)$_2$Cl$_2$:CuI:MeCN:Et$_3$N is 1:1.5:4:0.05:0.1:3.

Scheme II

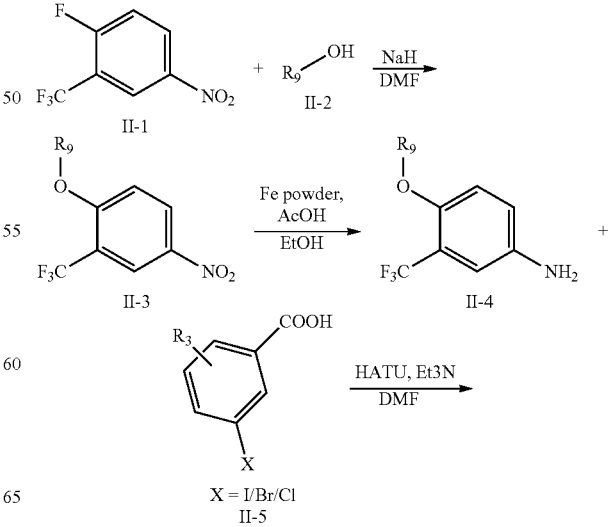

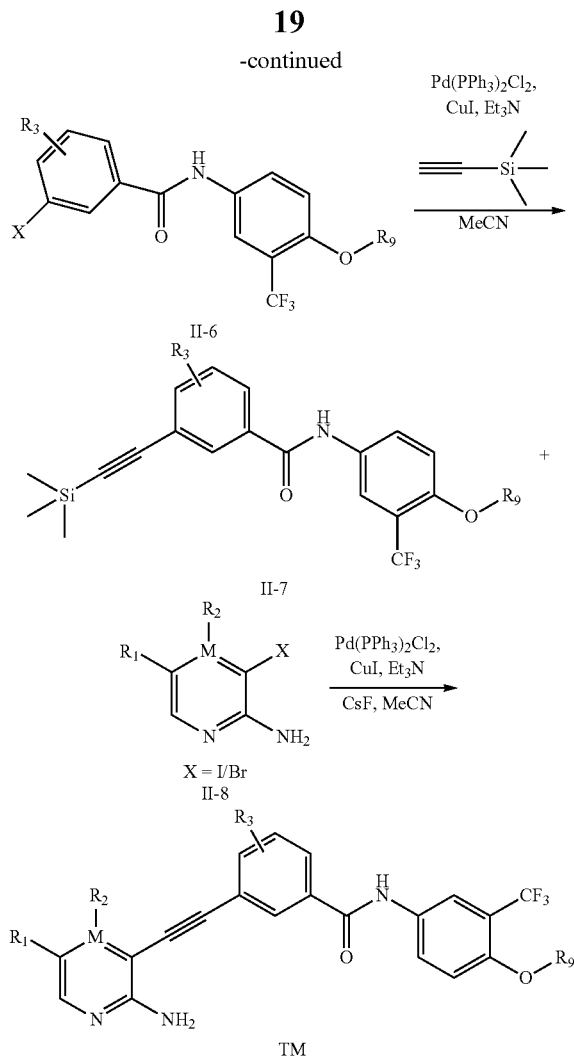

Scheme II comprises the following steps:

Step 1: compound II-2 and NaH are added into a round-bottom flask and DMF is used as a solvent; the mixture is stirred at ice water bath for 30 min, then compound II-1 is added, and the reaction is carried out under room temperature for 12 hours, compound II-3 is obtained by purification; wherein the equivalent ratio of compound II-1:compound II-2:NaH is 1:1.2:1.5.

Step 2: compound II-3, Fe powder, AcOH and ethanol are added into a round-bottom flask, the mixture is reacted at 80° C. for 12 hours until completion, and the compound II-4 is obtained by purification; wherein the equivalent ratio of compound II-3:Fe powder:AcOH is 1:1.1:1.2.

Step 3: compound II-5, HATU, Et$_3$N and DMF are added into a round-bottom flask. After stirring under room temperature for 30 min, compound II-4 is added, and the mixture is stirred at room temperature for 12 hours until reaction is completed, compound II-6 is obtained by purification; wherein the equivalent ratio of compound II-6:HATU:Et$_3$N:compound II-5 is 1:2:2:0.9.

Step 5: compound II-6, trimethylsilylacetylene, Pd(PPh$_3$)$_2$Cl$_2$, CuI and Et$_3$N are added into a round-bottom flask and MeCN is used as a solvent, and the mixture is heated to 80° C. in oil bath for 12 hours until reaction is completed; the compound II-7 is obtained by purification; wherein the equivalent ratio of compound II-6:trimethylsilylacetylene:Pd(PPh$_3$)$_2$Cl$_2$:CuI:Et$_3$N is 1:1.5:0.05:0.1:3.

Step 6: compound II-7, compound II-8, cesium fluoride, Pd(PPh$_3$)$_2$Cl$_2$, CuI and Et$_3$N are added into a round-bottom flask and MeCN is used as a solvent, and the mixture is heated to 80° C. in oil bath for 12 hours until reaction is completed, and the compound TM is obtained by purification; wherein the equivalent ratio of compound II-7:compound II-8:cesium fluoride:Pd (PPh$_3$)$_2$Cl$_2$:CuI:MeCN:Et$_3$N is 1:1.5:4:0.05:0.1:3.

The present invention also provides a pharmaceutical composition comprising one or more of the above compounds of formula (I) or the deuterated compound, or the pharmaceutically acceptable salt or prodrug thereof, and a pharmaceutically acceptable excipient.

The present invention also provides the use of the above formula (I) compound or the deuterated compound, or the pharmaceutically acceptable salt or the prodrug thereof, or the above pharmaceutical composition in preparation of FGFR kinase inhibitor, RET kinase inhibitor and/or inhibitor for mutant of FGFR or RET kinases.

The present invention also provides the use of the above compound of the formula (I) or the deuterated compound, or pharmaceutically acceptable salt or prodrug thereof, or the above pharmaceutical composition in preparing a medicament for treating tumor; optionally, the tumor comprises non-small cell lung cancer, breast cancer, thyroid cancer (medullary thyroid carcinoma, papillary thyroid cancer), gastric cancer, bladder cancer, endometrial cancer, prostate cancer, cervical cancer, colon cancer, esophageal cancer, keratinoma, myeloma, rhabdomyosarcoma, acute leukemia, liver cancer, adenocarcinoma, and pancreatic cancer.

The present invention also provides the use of the above compound of formula (I) or the deuterated compound thereof, or pharmaceutically acceptable salt or prodrug thereof, or the above pharmaceutical composition in treating tumor. Optionally, the tumor comprises non-small cell lung cancer, breast cancer, thyroid cancer (medullary thyroid carcinoma, papillary thyroid cancer), gastric cancer, bladder cancer, endometrial cancer, prostate cancer, cervical cancer, colon cancer, esophageal cancer, keratinoma, myeloma, rhabdomyosarcoma, acute leukemia, liver cancer, adenocarcinoma, and pancreatic cancer.

According to an embodiment of the present invention, the o-aminoheteroarylalkynyl-containing compound has an advantage of high dual-targeting inhibitory activity on FGFR and RET.

According to another embodiment of the present invention, the o-aminoheteroarylalkynyl-containing compound has an advantage of low KDR activity.

According to another embodiment of the present invention, the o-aminoheteroarylalkynyl-containing compound exhibits strong inhibition of cell proliferation activity in human lung cancer NCI-H1581, gastric cancer cell line SNU16 and RET-dependent sensitive cell line BaF3-CCDC6-Ret and mutants thereof.

According to another embodiment of the present invention, the pharmacokinetic data indicate that the o-aminoheteroarylalkynyl-containing compound has good druggability and exhibits significant inhibitory activity on tumor growth in a long-term animal pharmacodynamic model.

According to another embodiment of the present invention, the animal is in good condition (including no significant decrease in body weight) at the effective dose, and no significant toxicity of other RTK multi-target inhibitors is observed (no animal death and molting).

DRAWINGS

FIG. 1 is a Western blot diagram of the pharmacological experiment example 2 which shows that the compounds HuFGFR267, HuFGFR293 and the positive control Ponatinib inhibit RET kinase phosphorylation and the downstream signaling pathways in tumor cells, wherein P-RET is phosphorylated RET kinase, P-AKT is phosphorylated AKT kinase, P-ErK is phosphorylated ErK kinase, GAPDH is glyceraldehyde-3-phosphate dehydrogenase, and ACTIN is actin.

FIG. 2 is a line diagram of the pharmacological experiment Example 3 which shows the inhibitory effect of the compounds HuFGFR267 and AZD4547 on growth of human lung cancer NCI-H1581 xenografts in nude mice, wherein in t student's test ***$p<0.001$ when compared with solvent control group.

FIG. 3 is a line diagram of the pharmacological experiment example 3 which shows that the effects of the compounds HuFGFR267 and AZD4547 on the body weight of mice bearing human lung cancer NCI-H1581 tumor.

EMBODIMENTS FOR CARRYING OUT THE INVENTION

Figure 4:
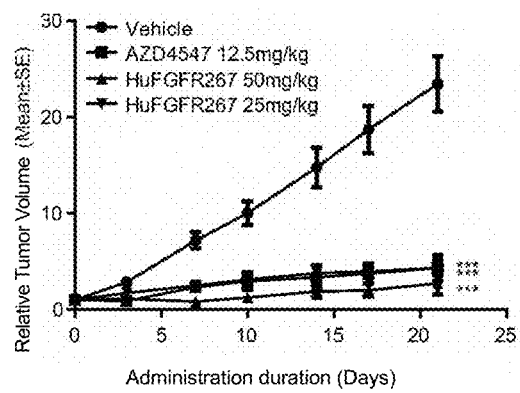
FIG. 4 is a line diagram of the pharmacological experiment example 3 which shows that the inhibitory effect of the compounds HuFGFR267 and AZD4547 on growth of subcutaneous human gastric cancer SNU-16 xenografts in nude mice, wherein in t student's test, ***$p<0.001$ when compared with solvent control group.

Specific embodiments of the present invention will be described in detail below. It should be understood that the specific embodiments described herein are illustrative of the invention and are not intended to limit the invention.

PREPARATION EXAMPLE

Example 1. Preparation of HuFGFR267

Step One:

2-methyl-5-nitrobenzotrifluoride (1 g, 5 mmol), NBS (980 mg, 5.5 mmol), AIBN (164 mg, 1 mmol) and $CCl_4$ (20 ml) were added into a round-bottom flask and the reaction was carried out by heating in an oil bath under 100° C. for 36 hours until completion. The mixture was cooled to room temperature, the solvent was removed under reduced pressure. After column chromatography, the product 2-trifluoromethyl-4-nitrobenzyl bromide was obtained (1.04 g, yield: 70%).

Step Two:

2-trifluoromethyl-4-nitrobenzyl bromide (849 mg, 3 mmol), N-methylpiperazine (330 mg, 3.3 mmol), $Et_3N$ (364 mg, 3.6 mmol) and $CH_2Cl_2$ (10 ml) were added into a round-bottom flask, and the reaction was carried out at room temperature for 12 hours until completion. The solvent was removed under vacuo. After column chromatography, the product 1-methyl-4-(4-nitro-2-(trifluoromethyl)benzyl)piperazine is obtained (901 mg, yield: 97%).

Step Three:

1-methyl-4-(4-nitro-2-(trifluoromethyl)benzyl)piperazine (901 mg, about 3 mmol), reducing Fe powder (672 mg, 12 mmol), $NH_4Cl$ (318 mg, 6 mmol), EtOH (15 ml) were added into a round bottom flask; and the reaction was carried out at 80° C. in an oil bath for 10 hours until completion. After filtration via a pad of celite, the filtrate was concentrated under reduced pressure. The product 4-((4-methyl piperazin-1-yl)methylene)-3-(trifluoromethyl)aniline (754 mg, yield: 91%) was obtained by column chromatography.

Step Four:

3-iodo-4-chlorobenzoic acid (1 g, 3.55 mmol), $Et_3N$ (574 mg, 7.1 mmol), HATU (2.7 g, 7.1 mmol), DMF (50 ml) were added into a round-bottom flask. After stirring at room temperature for 0.5 hour, 4-((4-methylpiperazin-1-yl)methylene)-3-(trifluoromethyl)aniline (776 mg, 2.84) was added. The reaction was carried out at room temperature for 6 hours until completion, and the solvent was removed under reduced pressure. 3-iodo-4-chloro-N-(4-((4-methylpiperazin-1-yl)methylene)-3-(trifluoromethyl)phenyl)benzamide (1.5 g, yield: 98%) was obtained by column chromatography.

Step Five:

3-iodo-4-chloro-N-(4-((4-methylpiperazin-1-yl)methylene)-3-(trifluoromethyl)phenyl)benzamide (537 mg, 1 mmol), trimethylsilylacetylene (147 mg, 1.5 mmol), Pd $(PPh_3)_2Cl_2$ (60 mg, 0.05 mmol), CuI (20 mg, 0.1 mmol), $Et_3N$ (404 mg, 4 mmol)) and MeCN (40 mL) were added into a round-bottom flask, and the mixture was heated to 70° C. in oil bath and reacted overnight until the reaction was completed. After column chromatography, the product 4-chloro-N-(4-((4-methylpiperazin-1-yl)methylene)-3-(trifluoromethyl)phenyl)-3-((trimethylsilyl)ethynyl)benzamide was obtained (466 mg, yield: 92%).

Step Six:

4-chloro-N-(4-((4-methylpiperazin-1-yl)methylene)-3-(trifluoromethyl)phenyl)-3-((Trimethylsilyl)ethynyl)benzamide (320 mg, 0.63 mmol), 2-amino-3-iodopyridine (165 mg, 0.75 mmol), Pd $(PPh_3)_2Cl_2$ (22 mg, 0.032 mmol), CuI (13 mg, 0.063 mmol), CsF (383 mg, 2.52 mmol), $Et_3N$ (254.5 mg, 2.52 mmol) and MeCN (40 mL) were added into a round-bottom flask, and mixture was heated to 70° C. in oil bath and reacted overnight until the reaction was completed. After column chromatography, the product 3-(2-aminopyridine-3-ethynyl)-4-chloro-N-(4-((4-methylpiperazin-1-yl)methylene)-3-(trifluoromethyl)phenyl)benzamide (huGFR267) was obtained (305 mg, yield: 92%).

$^1$H NMR (400 MHz, $CD_3OD$) δ 8.24 (d, J=2.2 Hz, 1H), 8.13 (d, J=2.2 Hz, 1H), 8.00 (s, 1H), 7.93 (d, J=2.2 Hz, 1H), 7.91 (d, J=2.2 Hz, 1H), 7.76 (d, J=8.5 Hz, 1H), 7.70 (dd, J=7.5, 1.6 Hz, 1H), 7.65 (d, J=8.5 Hz, 1H), 6.70 (dd, J=7.4, 5.1 Hz, 1H), 3.64 (d, J=18.7 Hz, 2H), 2.55 (s, 8H), 2.33 (s, 3H). LR-MS (ESI) m/z 528 (M+1).

Example 2. Preparation of HuFGFR302

The synthesis method was carried out as Example 1, except that 3-iodo-4-fluorobenzoic acid was used instead of 3-iodo-4-chlorobenzoic acid.

$^1$H NMR (400 MHz, $CD_3OD$) δ 8.26 (dd, J=6.7, 2.3 Hz, 1H), 8.14 (d, J=2.2 Hz, 1H), 8.08-7.92 (m, 3H), 7.79 (d, J=8.5 Hz, 1H), 7.71 (dd, J=7.5, 1.8 Hz, 1H), 7.38 (t, J=8.9

Hz, 1H), 6.71 (dd, J=7.5, 5.1 Hz, 1H), 3.69 (s, 2H), 2.59 (s, 8H), 2.40 (s, 3H). LR-MS (ESI) m/z 512 (M+1).

Example 3. Preparation of HuFGFR301

The synthesis method was carried out as Example 1, except that 3-iodo-4-methylbenzoic acid was used instead of 3-iodo-4-chlorobenzoic acid.
$^1$H NMR (400 MHz, CD$_3$OD) δ 8.20-8.11 (m, 2H), 8.00-7.92 (m, 2H), 7.86 (dd, J=7.9, 2.0 Hz, 1H), 7.75 (d, J=8.5 Hz, 1H), 7.68 (dd, J=7.5, 1.8 Hz, 1H), 7.42 (d, J=8.1 Hz, 1H), 6.68 (dd, J=7.5, 5.1 Hz, 1H), 3.70 (s, 2H), 2.94 (s, 4H), 2.64 (d, J=13.5 Hz, 7H), 2.57 (s, 3H). LR-MS (ESI) m/z 508 (M+1).

Example 4. Preparation of HuFGFR321

The synthesis method was carried out as Example 1, except that 3-iodo-4-methoxybenzoic acid was used instead of 3-iodo-4-chlorobenzoic acid.
$^1$H NMR (400 MHz, CDCl$_3$) δ 9.07 (s, 1H), 8.39 (d, J=3.0 Hz, 1H), 8.06 (d, J=3.0 Hz, 1H), 7.94 m, 2H), 7.70 (dd, J=15.0, 3.0 Hz, 1H), 7.56 (dd, J=15.0, 3.0 Hz, 1H), 7.37 (d, J=15.0 Hz, 1H), 7.08 (d, J=15.0 Hz, 1H), 6.54 (t, J=15.0 Hz, 1H), 3.92 (s, 3H), 3.54 (s, 2H), 2.54-2.42 (m, 4H), 2.34 (td, J=10.1, 1.7 Hz, 6H), 2.18 (d, J=30.2 Hz, 3H). LR-MS (ESI) m/z 524 (M+1).

Example 5. Preparation of HuFGFR322

The synthesis method was carried out as Example 1, except that 3-iodo-4-cyanobenzoic acid was used instead of 3-iodo-4-chlorobenzoic acid.
$^1$H NMR (400 MHz, CDCl$_3$) δ 9.07 (s, 1H), 8.57 (d, J=3.0 Hz, 1H), 8.07 (dt, J=5.9, 3.0 Hz, 2H), 7.97 (dd, J=15.0, 3.0 Hz, 1H), 7.80 (d, J=15.0 Hz, 1H), 7.70 (dd, J=15.0, 3.0 Hz, 1H), 7.56 (dd, J=15.0, 3.0 Hz, 1H), 7.37 (d, J=15.0 Hz, 1H), 6.54 (t, J=15.0 Hz, 1H), 3.54 (s, 2H), 2.56-2.44 (m, 4H), 2.42 (s, 2H), 2.40-2.30 (m, 4H), 2.18 (d, J=30.2 Hz, 3H). LR-MS (ESI) m/z 519 (M+1).

Example 6. Preparation of HuFGFR293

The synthesis method was carried out as Example 1, except that 3-iodobenzoic acid was used instead of 3-iodo-4-chlorobenzoic acid.
$^1$H NMR (400 MHz, CD$_3$OD) δ 8.17 (t, J=1.5 Hz, 1H), 8.15 (d, J=2.2 Hz, 1H), 7.99-7.92 (m, 3H), 7.79-7.73 (m, 2H), 7.66 (dd, J=7.5, 1.8 Hz, 1H), 7.53 (t, J=7.8 Hz, 1H), 6.66 (dd, J=7.5, 5.1 Hz, 1H), 3.67 (s, 2H), 2.64 (d, J=45.5 Hz, 8H), 2.43 (s, 3H). LR-MS (ESI) m/z 494 (M+1).

Example 7. Preparation of HuFGFR315

The synthesis method was carried out as Example 1, except that 3-iodo-5-fluorobenzoic acid was used instead of 3-iodo-4-chlorobenzoic acid.
$^1$H NMR (400 MHz, CD$_3$OD) δ 8.14 (d, J=2.1 Hz, 1H), 8.00 (t, J=1.4 Hz, 1H), 8.00-7.92 (m, 2H), 7.75 (d, J=8.5 Hz, 1H), 7.73-7.65 (m, 2H), 7.55 (ddd, J=8.9, 2.5, 1.3 Hz, 1H), 6.66 (dd, J=7.5, 5.1 Hz, 1H), 3.68 (s, 2H), 2.67 (d, J=60.6 Hz, 8H), 2.48 (s, 3H). LR-MS (ESI) m/z 512 (M+1).

Example 8. Preparation of HuFGFR314

The synthesis method was carried out as Example 1, except that 2-fluoro-5-iodobenzoic acid was used instead of 3-iodo-4-chlorobenzoic acid.
$^1$H NMR (400 MHz, DMSO) δ 10.83 (s, 1H), 8.17 (d, J=1.9 Hz, 1H), 8.05 (dd, J=6.8, 2.2 Hz, 1H), 8.02-7.92 (m, 2H), 7.86 (ddd, J=8.6, 4.9, 2.2 Hz, 1H), 7.73 (d, J=8.5 Hz, 1H), 7.61 (dd, J=7.5, 1.9 Hz, 1H), 7.45 (dd, J=9.8, 8.7 Hz, 1H), 6.58 (dd, J=7.5, 4.9 Hz, 1H), 6.44 (s, 2H), 3.61 (s, 2H), 2.60 (s, 4H), 2.51-2.39 (m, 4H), 2.35 (s, 3H). LR-MS (ESI) m/z 512 (M+1).

Example 9. Preparation of HuFGFR327

The synthesis method was carried out as Example 1, except that 3-iodo-5-chlorobenzoic acid was used instead of 3-iodo-4-chlorobenzoic acid.
$^1$H NMR (400 MHz, CDCl$_3$) δ 9.11 (s, 1H), 8.27 (t, J=3.0 Hz, 1H), 8.06 (d, J=3.0 Hz, 1H), 7.97 (dd, "J=15.0, 3.0 Hz, 1H), 7.84 (dt, J=8.0, 3.0 Hz, 2H), 7.70 (dd, J=15.0, 3.0 Hz, 1H), 7.56 (dd, J=15.0, 3.0 Hz, 1H), 7.37 (d, J=15.0 Hz, 1H), 6.54 (t, J=15.0 Hz, 1H), 3.54 (s, 2H), 2.52-2.44 (m, 4H)), 2.42-2.26 (m, 4H), 2.21 (s, 2H), 2.18 (s, 3H). LR-MS (ESI) m/z 528 (M+1).

Example 10. Preparation of HuFGFR329

The synthesis method was carried out as Example 1, except that 3-iodo-5-trifluoromethylbenzoic acid was used instead of 3-iodo-4-chlorobenzoic acid.
$^1$H NMR (400 MHz, CDCl$_3$) δ 9.09 (s, 1H), 8.39 (t, J=3.0 Hz, 1H), 8.10 (ddd, J=17.4, 10.2, 3.0 Hz, 3H), 7.97 (Dd, J=14.9, 3.0 Hz, 1H), 7.70 (dd, J=15.0, 3.0 Hz, 1H), 7.56 (dd, J=15.0, 2.9 Hz, 1H), 7.37 (d, J=15.0 Hz, 1H), 6.54 (t, J=15.0 Hz, 1H), 3.54 (s, 2H), 2.57-2.43 (m, 4H), 2.39-2.29 (m, 4H), 2.10 (s, 5H). LR-MS (ESI) m/z 562 (M+1).

Example 11. Preparation of HuFGFR330

The synthesis method was carried out as Example 1, except that 3-iodo-5-cyanobenzoic acid was used instead of 3-iodo-4-chlorobenzoic acid.
$^1$H NMR (400 MHz, CDCl$_3$) δ 9.06 (s, 1H), 8.67 (t, J=3.0 Hz, 1H), 8.55 (t, J=3.0 Hz, 1H), 8.21-8.01 (m, 2H), 7.97 (dd, J=14.9, 3.1 Hz, 1H), 7.70 (dd, J=15.0, 3.0 Hz, 1H), 7.56 (dd, J=14.9, 2.9 Hz, 1H), 7.37 (d, J=15.0 Hz, 1H), 6.54 (t, J=15.0 Hz, 1H), 3.54 (s, 2H), 2.54-2.43 (m, 4H), 2.38-2.28 (m, 4H), 2.15 (s, 2H), 2.13 (s, 3H). LR-MS (ESI) m/z 519 (M+1).

Example 12. Preparation of HuFGFR331

The synthesis method was carried out as Example 1, except that 3-iodo-5-methylbenzoic acid was used instead of 3-iodo-4-chlorobenzoic acid.
$^1$H NMR (400 MHz, CDCl$_3$) δ 9.09 (s, 1H), 8.29 (t, J=3.0 Hz, 1H), 8.06 (d, J=3.0 Hz, 1H), 7.97 (dd, "J=14.9, 3.1 Hz, 1H), 7.81 (dt, J=16.3, 3.0 Hz, 2H), 7.70 (dd, J=15.0, 3.0 Hz, 1H), 7.56 (dd, J=14.9, 2.9 Hz, 1H), 7.37 (d, J=15.0 Hz, 1H), 6.54 (t, J=15.0 Hz, 1H), 3.54 (s, 2H), 2.54-2.44 (m, 4H), 2.39-2.29 (m, 7H), 2.14 (s, 3H). LR-MS (ESI) m/z 508 (M+1).

Example 13. Preparation of HuFGFR332

The synthesis method was carried out as Example 1, except that 3-iodo-5-methoxybenzoic acid was used instead of 3-iodo-4-chlorobenzoic acid.
$^1$H NMR (400 MHz, CDCl$_3$) δ 9.14 (s, 1H), 8.07 (d, J=4.0 Hz, 2H), 7.97 (s, 1H), 7.88 (s, 1H), 7.70 (s, 1H), 7.56 (s, 1H), 7.37 (s, 1H), 6.75 (s, 1H), 6.54 (s, 1H), 3.79 (s, 3H), 3.54 (s, 2H), 2.48 (s, 4H), 2.34 (s, 4H), 2.18 (s, 2H), 2.10 (s, 3H). LR-MS (ESI) m/z 524 (M+1).

Example 14. Preparation of HuFGFR333

The synthesis method was carried out as Example 1, except that 2-methyl-5-iodobenzoic acid was used instead of 3-iodo-4-chlorobenzoic acid.

$^1$H NMR (400 MHz, CDCl$_3$) δ 8.77 (s, 1H), 8.34 (s, 1H), 8.06 (s, 1H), 7.97 (s, 1H), 7.80-7.51 (m, 3H), 7.37 (s, 2H), 6.54 (s, 1H), 3.54 (s, 2H), 2.48 (s, 4H), 2.34 (s, 4H), 2.22 (s, 3H), 2.14 (s, 3H), 2.00 (s, 2H)). LR-MS (ESI) m/z 508 (M+1).

Example 15. Preparation of HuFGFR334

The synthesis method was carried out as Example 1, except that 2-methoxy-5-iodobenzoic acid was used instead of 3-iodo-4-chlorobenzoic acid.

$^1$H NMR (400 MHz, CDCl$_3$) δ 9.49 (s, 1H), 8.39 (s, 1H), 8.06 (s, 1H), 7.97 (s, 1H), 7.69 (d, J=4.0 Hz, 2H), 7.56 (s, 1H), 7.37 (s, 1H), 7.08 (s, 1H), 6.54 (s, 1H), 3.93 (s, 3H), 3.54 (s, 2H), 2.48 (s, 4H), 2.34 (s, 4H), 2.21 (s, 2H), 2.14 (s, 3H). LR-MS (ESI) m/z 524 (M+1).

Example 16. Preparation of HuFGFR355

The synthesis method was carried out as Example 1, except that 2-amino-3-iodo-5-fluoropyridine was used instead of 2-amino-3-iodopyridine.

$^1$H NMR (400 MHz, CD$_3$OD) δ 8.26 (d, J=2.2 Hz, 1H), 8.15 (d, J=2.1 Hz, 1H), 7.95 (ddt, J=18.6, 12.3, 6.0 Hz, 3H), 7.76 (d, J=8.5 Hz, 1H), 7.64 (d, J=8.5 Hz, 1H), 7.52 (dd, J=8.3, 2.8 Hz, 1H), 3.72 (s, 2H), 2.83 (m, 11H). LR-MS (ESI) m/z 546 (M+1).

Example 17. Preparation of HuFGFR356

The synthesis method was carried out as Example 1, except that 2-amino-3-iodo-5-chloropyridine was used instead of 2-amino-3-iodopyridine.

$^1$H NMR (400 MHz, CDCl$_3$) δ 9.07 (s, 1H), 8.33 (s, 1H), 8.04 (d, J=12.5 Hz, 2H), 7.89 (d, J=12.0 Hz, 2H), 7.55 (d, J=8.0 Hz, 2H), 7.37 (s, 1H), 3.54 (s, 2H), 2.64 (s, 2H), 2.48 (s, 4H), 2.34 (s, 4H), 2.13 (s, 3H). LR-MS (ESI) m/z 562 (M+1).

Example 18. Preparation of HuFGFR357

The synthesis method was carried out as Example 1, except that 2-amino-3-iodo-5-methylpyridine was used instead of 2-amino-3-iodopyridine.

$^1$H NMR (400 MHz, DMSO) δ 8.33 (s, 1H), 8.06 (s, 1H), 7.86 (d, J=20.0 Hz, 2H), 7.57 (d, J=4.0 Hz, 2H), 7.30 (d, J=8.0 Hz, 2H), 6.89 (s, 2H), 3.54 (s, 2H), 2.48 (s, 4H), 2.34 (s, 4H), 2.23 (s, 3H), 2.19 (s, 3H). LR-MS (ESI) m/z 542 (M+1).

Example 19. Preparation of HuFGFR358

The synthesis method was carried out as Example 1, except that 2-amino-3-iodo-5-cyclopropylpyridine was used instead of 2-amino-3-iodopyridine.

$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.78 (d, J=2.9 Hz, 1H), 7.65-7.52 (m, 2H), 7.30 (dd, J=8.9, 7.4 Hz, 2H), 6.89 (s, 2H), 3.54 (s, 2H), 2.50 (ddd, J=24.7, 19.4, 10.9 Hz, 4H), 2.41-2.28 (m, 4H), 2.18 (d, J=30.1 Hz, 3H), 1.86-1.52 (m, 1H), 1.39-0.82 (m, 4H). LR-MS (ESI) m/z 568 (M+1).

Example 20. Preparation of HuFGFR307

The synthesis method was carried out as Example 1, except that 2-amino-3-iodo-5-trifluoromethylpyridine was used instead of 2-amino-3-iodopyridine.

$^1$H NMR (400 MHz, CD$_3$OD) δ 8.26 (d, J=2.1 Hz, 2H), 8.13 (d, J=2.0 Hz, 1H), 7.92 (dd, J=13.3, 4.8 Hz, 2H), 7.85 (d, J=2.2 Hz, 1H), 7.73 (d, J=8.5 Hz, 1H), 7.60 (d, J=8.4 Hz, 1H), 3.68 (s, 2H), 2.85 (s, 4H), 2.59 (d, J=28.5 Hz, 7H). LR-MS (ESI) m/z 596 (M+1).

Example 21. Preparation of HuFGFR359

The synthesis method was carried out as Example 1, except that 2-amino-3-iodo-5-cyanopyridine was used instead of 2-amino-3-iodopyridine.

NMR 8.400 (d, J=2.9 Hz, 1H), 7.95-7.83 (m, 2H), 7.64-7.49 (m, 2H), 7.31 (d, J=15.0 Hz, 1H), 6.89 (s, 2H), 3.54 (s, 2H), 2.57-2.44 (m, 4H), 2.41-2.31 (m, 4H), 2.11 (s, 3H). LR-MS (ESI) m/z 553 (M+1).

Example 22. Preparation of HuFGFR360

The synthesis was carried out as Example 1, except that 2-amino-3-iodo-5-methoxypyridine was used instead of 2-amino-3-iodopyridine.

NMR 8.50 (s, 1H), 8.04 (s, 1H) (d, J=16.0 Hz, 2H), 3.91 (s, 3H), 3.53 (s, 2H), 2.47 (s, 3H), 2.33 (s, 3H), 2.13 (s, 3H). LR-MS (ESI) m/z 558 (M+1).

Example 23. Preparation of HuFGFR361

The synthesis method was carried out as Example 1, except that 2-amino-3-iodo-5-trifluoromethoxypyridine was used in place of 2-amino-3-iodopyridine.

$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.64 (d, J=2.9 Hz, 1H), 7.61-7.53 (m, 2H), 7.46 (d, J=3.1 Hz, 1H), 7.31 (d, J=15.0 Hz, 1H), 6.89 (s, 2H), 3.54 (s, 2H), 2.54-2.43 (m, 4H), 2.42-2.29 (m, 4H), 2.18 (d, J=30.1 Hz, 3H). LR-MS (ESI) m/z 612 (M+1).

Example 24. Preparation of HuFGFR362

The synthesis was carried out as Example 1, except that 2-amino-3-iodo-5-cyclopropyloxypyridine was used instead of 2-amino-3-iodopyridine.

$^1$H NMR (400 MHz, DMSO) δ 8.30 (d, J=2.9 Hz, 1H), 8.04 (d, J=2.9 Hz, 1H), 7.86 (dd, J=14.9, 2.9 Hz, 1H), 7.62 (d, J=3.1 Hz, 1H), 7.59-7.49 (m, 2H), 7.34 (d, J=2.9 Hz, 1H), 7.29 (d, J=15.0 Hz, 1H), 6.87 (s, 2H), 3.53 (s, 2H), 3.44-3.21 (m, 1H), 2.49 (ddd, J=24.6, 18.7, 12.1 Hz, 4H), 2.39-2.26 (m, 4H), 2.13 (s, 3H), 0.71-0.28 (m, 2H), 0.28--0.20 (m, 2H). LR-MS (ESI) m/z 584 (M+1).

Example 25. Preparation of HuFGFR363

The synthesis was carried out as Example 1, except that 2-amino-3-iodo-5-(3-oxetanyl)oxypyridine was used instead of 2-amino-3-iodopyridine.

$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.58 (ddd, J=14.9, 13.4, 3.0 Hz, 3H), 7.31 (d, J=15.0 Hz, 1H), 6.89 (s, 2H), 4.04 (d, J=2.9 Hz, 1H), 3.54 (s, 2H), 2.50 (ddd, J=24.7, 19.4, 10.9 Hz, 4H), 2.38-2.27 (m, 4H), 2.11 (s, 3H). LR-MS (ESI) m/z 600 (M+1).

Example 26. Preparation of HuFGFR377

The synthesis method was carried out as Example 1, except that 2-amino-3-iodo-5-(2-hydroxyethyl)oxypyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.58 (ddd, J=14.9, 13.4, 2.9 Hz, 3H), 7.33 (dd, J=18.3, 9.0 Hz, 2H), 6.89 (s, 2H), 4.90 (s, 1H), 4.33 (td, J=14.5, 0.5 Hz, 2H), 3.68 (dd, J=21.5, 7.4 Hz, 2H), 3.54 (s, 2H), 2.59-2.40 (m, 4H), 2.40-2.28 (m, 4H), 2.10 (s, 3H). LR-MS (ESI) m/z 588 (M+1).

Example 27. Preparation of HuFGFR378

The synthesis was carried out as Example 1, except that 2-amino-3-iodo-5-(2-methoxyethyl)oxypyridine was used instead of 2-amino-3-iodopyridine.
NMR 8.400 (d, J=2.9 Hz, 1H), 1H), 7.57 (ddd, J=14.9, 13.4, 3.0 Hz, 3H), 7.32 (dd, J=17.7, 8.9 Hz, 2H), 6.88 (s, 2H), 4.30 (td, J=14.5, 0.7 Hz, 2H), 3.76 (td, J=14.6, 0.8 Hz, 2H), 3.53 (s, 2H), 3.40 (s, 3H), 2.59-2.43 (m, 4H), 2.43-2.25 (m, 4H), 2.19 (s, 3H). LR-MS (ESI) m/z 602 (M+1).

Example 28. Preparation of HuFGFR379

The synthesis method was carried out as Example 1, except that 2-amino-3-iodo-5-(2-methylaminoethyl)oxypyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.58 (ddd, J=14.9, 13.4, 2.9 Hz, 3H), 7.33 (dd, J=14.4, 9.0 Hz, 2H), 6.89 (s, 2H), 4.13 (t, J=14.6 Hz, 2H), 3.54 (s, 2H), 3.26 (s, 3H), 3.01 (t, J=14.6 Hz, 2H), 2.60-2.43 (m, 4H), 2.42-2.26 (m, 4H), 2.14 (s, 3H), 1.84 (s, 1H). LR-MS (ESI) m/z 601 (M+1).

Example 29. Preparation of HuFGFR380

The synthesis was carried out as Example 1, except that 2-amino-3-iodo-5-(2-dimethylaminoethyl)oxypyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.64 (d, J=2.9 Hz, 1H), 7.62-7.57 (m, 1H), 7.57-7.53 (m, 1H), 7.36 (d, J=2.9 Hz, 1H), 7.31 (d, J=15.0 Hz, 1H), 6.89 (s, 2H), 4.07 (t, J=14.4 Hz, 2H), 3.54 (s, 2H), 2.72 (t, J=14.4 Hz, 2H), 2.52-2.44 (m, 4H), 2.38-2.30 (m, 4H), 2.27 (s, 6H), 2.14 (s, 3H). LR-MS (ESI) m/z 615 (M+1).

Example 30. Preparation of HuFGFR384

The synthesis method was carried out as Example 1, except that 2-amino-3-iodo-5-hydroxymethylpyridine was used instead of 2-amino-3-iodopyridine.
$^1$H NMR (500 MHz, CD$_3$OD) δ 8.33 (s, 1H), 8.06 (s, 1H), 7.89 (d, J=15.0 Hz, 2H), 7.58-7.46 (m, 3H), 7.37 (s, 1H), 4.61 (s, 2H), 3.54 (s, 2H), 2.48 (s, 3H), 2.34 (s, 3H), 2.17 (s, 3H). LR-MS (ESI) m/z 558 (M+1).

Example 31. Preparation of HuFGFR385

The synthesis method was carried out as Example 1, except that 2-amino-3-iodo-5-methoxymethylpyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.91 (d, J=2.9 Hz, 1H), 7.90-7.85 (m, 1H), 7.62-7.53 (m, 2H), 7.50 (d, J=2.9 Hz, 1H), 7.31 (d, J=15.0 Hz, 1H), 6.89 (s, 2H), 4.80 (s, 2H), 3.54 (s, 2H), 3.28 (s, 3H), 2.52-2.45 (m, 4H), 2.39-2.30 (m, 4H), 2.14 (s, 3H). LR-MS (ESI) m/z 572 (M+1).

Example 32. Preparation of HuFGFR386

The synthesis method was carried out as Example 1, except that 2-amino-3-iodo-5-trifluoromethoxymethylpyridine was used instead of 2-amino-3-iodopyridine.
$^1$H NMR (400 MHz, DMSO) δ 8.30 (d, J=2.9 Hz, 1H), 8.03 (d, J=2.9 Hz, 1H), 7.91-7.82 (m, 2H), 7.59-7.45 (m, 3H), 7.28 (d, J=14.9 Hz, 1H), 6.87 (s, 2H), 4.78 (s, 2H), 3.53 (s, 2H), 2.53-2.41 (m, 4H), 2.40-2.25 (m, 4H), 2.17 (d, J=30.1 Hz, 3H). LR-MS (ESI) m/z 626 (M+1).

Example 33. Preparation of HuFGFR387

The synthesis method was carried out as Example 1, except that 2-amino-3-iodo-5-methylaminomethylpyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.96 (d, J=3.1 Hz, 1H), 7.88 (dd, J=14.9, 2.9 Hz, 1H), 7.61-7.45 (m, 3H), 7.31 (d, J=15.0 Hz, 1H), 6.89 (s, 2H), 3.76 (s, 2H), 3.54 (s, 2H), 3.26 (s, 3H), 2.58-2.44 (m, 4H), 2.44-2.26 (m, 4H), 2.14 (s, 3H), 1.98 (s, 1H). LR-MS (ESI) m/z 571 (M+1).

Example 34. Preparation of HuFGFR388

The synthesis was carried out as Example 1, except that 2-amino-3-iodo-5-dimethylaminomethylpyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.96 (d, J=-3.1 Hz, 1H), 7.88 (dd, J=14.9, 2.9 Hz, 1H), 7.62-7.53 (m, 2H), 7.48 (d, J=3.1 Hz, 1H), 7.31 (d, J=15.0 Hz, 1H), 6.89 (s, 2H), 3.66 (s, 2H), 3.54 (s, 2H), 2.54-2.44 (m, 4H), 2.38-2.29 (m, 4H), 2.15 (d, J=8.1 Hz, 9H). LR-MS (ESI) m/z 585 (M+1).

Example 35. Preparation of HuFGFR389

The synthesis method was carried out as Example 1, except that 2-amino-3-iodo-5-methylaminopyridine was used instead of 2-amino-3-iodopyridine.
$^1$H NMR (400 MHz, DMSO) δ 8.33 (d, J=2.9 Hz, 1H), 8.06 (d, J=3.1 Hz, 1H), 7.88 (dd, J=14.9, 2.9 Hz, 1H), 7.68-7.43 (m, 2H), 7.31 (d, J=15.0 Hz, 1H), 7.11 (dd, J=8.9, 3.0 Hz, 2H), 6.89 (s, 2H), 5.88 (s, 1H), 3.54 (s, 2H), 2.68 (s, 3H), 2.58-2.41 (m, 4H), 2.40-2.28 (m, 4H), 2.14 (s, 3H). LR-MS (ESI)) m/z 557 (M+1).

Example 36. Preparation of HuFGFR390

The synthesis method was carried out as Example 1, except that 2-amino-3-iodo-5-dimethylaminopyridine was used instead of 2-amino-3-iodopyridine.
$^1$H NMR (400 MHz, DMSO) δ 8.33 (s, 1H), 8.06 (s, 1H), 7.88 (s, 1H), 7.57 (d, J=4.0 Hz, 2H), 7.31 (s, 1H), 7.11 (d, J=11.3 Hz, 2H), 6.89 (s, 2H), 3.54 (s, 2H), 2.92 (s, 6H), 2.48 (s, 4H), 2.34 (s, 4H), 2.24 (s, 3H). LR-MS (ESI) m/z 571 (M+1).

Example 37. Preparation of HuFGFR392

The synthesis method was carried out as Example 1, except that 2-amino-3-iodo-5-acetylaminopyridine was used instead of 2-amino-3-iodopyridine.

¹H NMR (400 MHz, CDCl₃) δ 9.10 (s, 1H), 8.38 (t, J=2.9 Hz, 1H), 8.05 (d, J=2.9 Hz, 1H), 7.98 (s, 1H), 7.92 (dt, J=14.6, 3.2 Hz, 1H), 7.81-7.69 (m, 2H), 7.63 (d, J=14.7 Hz, 1H), 7.59-7.47 (m, 2H), 7.36 (d, J=14.9 Hz, 1H), 3.53 (s, 2H), 2.52-2.43 (m, 4H), 2.40-2.31 (m, 4H), 2.23 (s, 2H), 2.14 (s, 3H)), 2.06 (s, 3H). LR-MS (ESI) m/z 551 (M+1).

Example 38. Preparation of HuFGFR396

The synthesis method was carried out as Example 1, except that 2-amino-3-iodo-5-(2-cyclopropylacetyl)aminopyridine was used instead of 2-amino-3-iodopyridine.

¹H NMR (400 MHz, CDCl₃) δ 9.10 (s, 1H), 8.39 (t, J=2.9 Hz, 1H), 8.30 (s, 1H), 8.06 (d, J=3.0 Hz, 1H), 7.93 (dt, J=14.6, 3.2 Hz, 1H), 7.80-7.69 (m, 2H), 7.68-7.50 (m, 3H), 7.37 (d, J=15.0 Hz, 1H), 3.54 (s, 2H), 2.55-2.42 (m, 4H), 2.41-2.30 (m, 4H), 2.23 (s, 1H), 2.22-2.00 (m, 4H), 1.02-0.40 (m, 4H). LR-MS (ESI) m/z 577 (M+1).

Example 39. Preparation of HuFGFR284

The synthesis method was carried out as Example 1, except that 2-amino-3-iodo-5-acrylamidopyridine was used instead of 2-amino-3-iodopyridine.

1H NMR (400 MHz, CDCl3) δ 9.08 (s, 1H), 9.05 (s, 1H), 8.31 (d, J=3.0 Hz, 1H), 8.04 (d, J=-3.0 Hz, 1H), 7.86 (dd, J=15.0, 3.0 Hz, 1H), 7.77 (d, J=3.0 Hz, 1H), 7.60-7.45 (m, 3H), 7.35 (d, J=15.0 Hz, 1H), 6.11 (m, 2H), 5.67 (dd, J=32.6, 5.2 Hz, 1H), 3.53 (s, 2H), 2.52-2.43 (m, 4H), 2.41-2.26 (m, 6H)), 2.13 (s, 3H). LR-MS (ESI) m/z 597 (M+1).

Example 40. Preparation of HuFGFR411

The synthesis method was carried out as Example 1, except that 2-amino-3-iodo-5-(4-dimethylamino-2-alkenylbutanoyl)aminopyridine was used instead of 2-amino-3-iodopyridine.

¹H NMR (400 MHz, CDCl₃) δ 9.06 (d, J=9.5 Hz, 2H), 8.33 (d, J=3.0 Hz, 1H), 8.06 (d, J=3.0 Hz, 1H), 7.88 (dd, J=15.0, 3.0 Hz, 1H), 7.79 (d, J=3.0 Hz, 1H), 7.60-7.49 (m, 3H), 7.37 (d, J=15.0 Hz, 1H), 6.79 (dt, J=30.2, 12.4 Hz, 1H), 5.57 (dt, J=30.2, 1.9 Hz, 1H), 3.54 (s, 2H), 3.02 (dd, J=12.4, 1.9 Hz, 2H), 2.75 (s, 6H), 2.55-2.44 (m, 4H), 2.43-2.26 (m, 6H), 2.14 (s, 3H). LR-MS (ESI) m/z 654 (M+1).

Example 41. Preparation of HuFGFR310

Step One:
Compound 1-methyl-4-piperidinol (1.26 g, 11 mmol) and NaH (240 mg, 12 mmol), were added into a round-bottom flask using DMF as a solvent. The mixture was stirred in ice water bath for 30 min, and 2-fluoro-5-nitrotrifluorotoluene (2.09 g, 10 mmol) was added, and the reaction was carried out at room temperature for 12 hours. The product 1-methyl-4-(4-nitro-2-(trifluoromethyl)phenylhydroxy)piperidine (2.9 g, yield: 95%) was obtained by purification.

Step Two:
Compound 1-methyl-4-(4-nitro-2-(trifluoromethyl)phenylhydroxy)piperidine (304 mg, 1 mmol), Fe powder (280 mg, 5 mmol), AcOH (1.2 g, 20 mmol), and ethanol (solvent) were added into a round-bottom flask, the reaction was carried out at 80° C. for 12 hours until completion, and the product 4-((1-methylpiperidinyl-4-yl)hydroxy)-3-(trifluoromethyl)aniline (261 mg., Yield: 95%) was obtained by purification.

Step Three:
3-iodo-4-fluorobenzoic acid (1 g, 3.55 mmol), Et₃N (574 mg, 7.1 mmol), and HATU (2.7 g, 7.1 mmol) were added into a round bottom flask, and DMF (50 ml) was added successively. After stirring at room temperature for 0.5 hr, 4-((1-methylpiperidinyl-4-yl)hydroxy)-3-(trifluoromethyl) aniline (778 mg, 2.84) was added, and the reaction was carried out at room temperature for 6 hours until completion. The solvent was evaporated to dryness under reduced pressure. After column chromatography, 4-chloro-3-iodo-N-(4-((1-methylpiperidinyl-4-yl)hydroxy)-3-(trifluoromethyl) phenyl)benzamide (1.77 g, yield: 93%) was obtained.

Step Four:
4-chloro-3-iodo-N-(4-((1-methylpiperidin-4-yl)hydroxy)-3-(trifluoromethyl)phenyl)benzamide (538 mg, 1 mmol)), trimethylsilylacetylene (147 mg, 1.5 mmol), Pd (PPh₃)₂Cl₂ (60 mg, 0.05 mmol), CuI (20 mg, 0.1 mmol), Et₃N (404 mg, 4 mmol)) and MeCN (40 mL) were added into a round-bottom flask, and the reaction was carried out overnight at 70° C. in oil bath until completion. After column chromatography, the product 4-chloro-N-(4-((1-methylpiperidin-4-yl)hydroxy)-3-(trifluoromethyl)phenyl-3-((trimethylsilyl)ethynyl)benzamide was obtained (477 mg, yield: 94%).

Step Five:
4-chloro-N-(4-((4-methylpiperazin-1-yl)methylene)-3-(trifluoromethyl)phenyl)-3-((trimethylsilyl)ethynyl)benzamide (320 mg, 0.63 mmol), 2-amino-3-iodopyridine (165 mg, 0.75 mmol), Pd (PPh₃)₂Cl₂ (22 mg, 0.032 mmol), CuI (13 mg, 0.063 mmol), CsF (383 mg, 2.52 mmol), Et₃N (254.5 mg, 2.52 mmol) and MeCN (40 mL) were added into a round-bottom flask, and the reaction was carried out overnight at 70° C. in oil bath until completion. After column chromatography, the product 3-(2-aminopyridine-3-ethynyl)-4-chloro-N-(4-((4-methylpiperazin-1-yl)methylene)-3-(trifluoromethyl)phenyl)-3-((trimethylsilyl)ethynyl) benzamide was obtained (301 mg, yield: 90%).

¹H NMR (400 MHz, CD₃OD) δ 8.24 (d, J=2.2 Hz, 1H), 8.04 (d, J=2.6 Hz, 1H), 8.00 (dd, J=5.1, 1.7 Hz, 1H), 7.91 (dt, J=9.0, 2.0 Hz, 2H), 7.71 (dd, J=7.5, 1.8 Hz, 1H), 7.65 (d, J=8.5 Hz, 1H), 7.26 (d, J=9.1 Hz, 1H), 6.70 (dd, J=7.5, 5.1 Hz, 1H), 4.81 (s, 1H), 3.04 (dd, J=15.6, 6.3 Hz, 4H), 2.69-2.64 (m, 3H), 2.14 (ddd, J=51.1, 16.4, 11.2 Hz, 4H). LR-MS (ESI) m/z 529 (M+1).

Example 42. Preparation of HuFGFR313

The synthesis method was carried out as Example 41, except that 3-iodo-4-fluorobenzoic acid was used instead of 3-iodo-4-chlorobenzoic acid.

¹H NMR (400 MHz, CD₃OD) δ 8.24 (dd, J=6.7, 2.4 Hz, 1H), 8.05 (d, J=2.6 Hz, 1H), 8.04-7.95 (m, 2H), 7.91 (Dd, J=9.0, 2.7 Hz, 1H), 7.68 (dd, J=7.5, 1.8 Hz, 1H), 7.33 (t, J=8.9 Hz, 1H), 7.28 (d, "J=9.1 Hz, 1H), 6.69 (dd, J=7.5, 5.1 Hz, 1H), 4.89-4.84 (m, 1H), 3.30-3.16 (m, 4H), 2.81 (s, 3H), 2.31-2.06 (m, 4H). LR-MS (ESI) m/z 513 (M+1).

Example 43. Preparation of HuFGFR402

The synthesis method was carried out as Example 41, except that 3-iodo-4-methylbenzoic acid was used instead of 3-iodo-4-chlorobenzoic acid.

¹H NMR (400 MHz, CDCl₃) δ 9.03 (s, 1H), 8.34 (d, J=3.0 Hz, 1H), 8.03 (d, J=3.0 Hz, 1H), 7.97 (dd, "J=15.0, 3.0 Hz, 1H), 7.82 (dd, J=15.0, 3.0 Hz, 1H), 7.70 (dd, J=15.0, 3.0 Hz, 1H), 7.55 (dd, J=15.0, 3.0 Hz, 1H), 7.37 (d, J=15.0 Hz, 1H), 6.81 (d, J=15.0 Hz, 1H), 6.54 (t, J=15.0 Hz, 1H), 3.83 (p,

J=14.7 Hz, 1H), 2.62-2.32 (m, 7H), 2.29-2.03 (m, 7H), 2.00-1.81 (m, 2H). LR-MS (ESI) m/z 509 (M+1).

Example 44. Preparation of HuFGFR403

The synthesis was carried out as Example 41, except that 3-iodo-4-methoxybenzoic acid was used instead of 3-iodo-4-chlorobenzoic acid.
$^1$H NMR (400 MHz, CDCl$_3$) δ 9.00 (s, 1H), 8.39 (d, J=3.0 Hz, 1H), 8.03 (d, J=3.0 Hz, 1H), 7.94 (m, 2H), 7.70 (dd, J=15.0, 3.0 Hz, 1H), 7.55 (dd, J=15.0, 3.0 Hz, 1H), 7.08 (d, J=15.0 Hz, 1H), 6.81 (d, J=15.0 Hz, 1H), 6.54 (t, J=15.0 Hz, 1H), 3.97-3.70 (m, 4H), 2.63-2.33 (m, 4H), 2.30 (s, 2H), 2.23-2.03 (m, 5H), 2.02-1.85 (m, 2H). LR-MS (ESI) m/z 525 (M+1).

Example 45. Preparation of HuFGFR312

The synthesis method was carried out as Example 41, except that 3-iodobenzoic acid was used instead of 3-iodo-4-chlorobenzoic acid.
$^1$H NMR (400 MHz, CD$_3$OD) δ 8.18 (t, J=1.5 Hz, 1H), 8.09 (d, J=2.6 Hz, 1H), 8.01-7.90 (m, 3H), 7.82-7.75 (m, 1H), 7.68 (dd, J=7.5, 1.8 Hz, 1H), 7.55 (t, J=7.8 Hz, 1H), 7.29 (d, J=9.1 Hz, 1H), 6.68 (dd, J=7.5, 5.1 Hz, 1H), 4.91-4.89 (m, 1H), 3.37-3.23 (m, 4H), 2.89 (s, 3H), 2.39-2.08 (m, 4H). LR-MS (ESI) m/z 495 (M+1).

Example 46. Preparation of HuFGFR268

The synthesis method was carried out as Example 1, except that 2-amino-3-iodopyrazine was used instead of 2-amino-3-iodopyridine.
$^1$H NMR (400 MHz, CD$_3$OD) δ 8.36 (d, J=2.2 Hz, 1H), 8.17 (d, J=2.1 Hz, 1H), 8.05 (d, J=2.4 Hz, 1H), 8.03-7.98 (m, 2H), 7.87 (s, 1H), 7.79 (d, J=8.5 Hz, 1H), 7.73 (d, J=8.5 Hz, 1H), 3.75 (s, 2H), 3.08 (s, 4H), 2.73 (s, 7H). LR-MS (ESI) m/z 529 (M+1).

Example 47. Preparation of HuFGFR463

The synthesis method was carried out as Example 1, except that 2-amino-3-iodo-5-fluoropyrazine was used instead of 2-amino-3-iodopyridine and 3-iodobenzoic acid was used instead of 3-iodo-4-chlorobenzoic acid.
$^1$H NMR (400 MHz, CDCl$_3$) δ 9.09 (s, 1H), 8.39 (t, J=2.9 Hz, 1H), 8.25 (d, J=16.0 Hz, 1H), 8.06 (d, J=3.0 Hz, 1H), 7.93 (dt, J=14.6, 3.2 Hz, 1H), 7.74 (dt, J=15.0, 3.2 Hz, 1H), 7.64 (d, J=14.7 Hz, 1H), 7.61-7.53 (m, 1H), 7.37 (d, J=15.0 Hz, 1H), 3.54 (s, 2H), 2.69-2.43 (m, 4H), 2.41-2.30 (m, 4H)), 2.18 (d, J"=30.2 Hz, 3H), 1.62 (s, 2H). LR-MS (ESI) m/z 513 (M+1).

Example 48. Preparation of HuFGFR464

The synthesis method was carried out as Example 1, except that 2-amino-3-iodo-5-hydroxymethylpyrazine was used instead of 2-amino-3-iodopyridine and 3-iodobenzoic acid was used instead of 3-iodo-4-chlorobenzoic acid.
NMR 8.40 (s, 1H), 8.26 (s, 1H) (s, 1H), 4.71 (s, 2H), 3.51 (s, 2H), 2.81 (s, 1H), 2.46 (s, 3H), 2.32 (s, 3H), 2.12 (s, 3H). LR-MS (ESI) m/z 525 (M+1).

Example 49. Preparation of HuFGFR452

The synthesis method was carried out as Example 1, except that 2-amino-3-iodo-4-fluoropyrazine was used instead of 2-amino-3-iodopyridine.

$^1$H NMR (400 MHz, CDCl$_3$) δ 9.08 (s, 1H), 8.33 (d, J=3.0 Hz, 1H), 8.06 (d, J=3.0 Hz, 1H), 7.92 (ddd, J=17.9, 15.0, 6.4 Hz, 2H), 7.60-7.48 (m, 2H), 7.37 (d, J=15.0 Hz, 1H), 6.51 (dd, J=15.9, 15.1 Hz, 1H), 5-MS (ESI) m/z 546 (M+1).

Example 50. Preparation of HuFGFR459

The synthesis was carried out as Example 1, except that 1-tert-butoxycarbonylpiperazine was used instead of N-methylpiperazine.
$^1$H NMR (400 MHz, CDCl$_3$) δ 8.33 (d, J=3.0 Hz, 1H), 8.07-7.81 (m, 3H), 7.70 (dd, J=15.0, 3.0 Hz, 1H), 7.60-7.48 (m, 2H), 7.31 (d, J=15.0 Hz, 1H), 6.89 (s, 2H), 6.53 (t, J=15.0 Hz, 1H), 3.54 (s, 2H), 3.19 (t, J=10.4 Hz, 4H), 2.48 (t, J=10.4 Hz, 4H), 1.42 (s, 9H). (ESI) m/z 614 (M+1).

Example 51. Preparation of HuFGFR472

HuFGFR459 (1.0 g, 1.75 mmol) was dissolved in anhydrous dichloromethane (20 mL), and trifluoroacetic acid (10 mL) was added dropwise into the solution under ice bath condition. The reaction was carried out in ice bath for 30 min. After purification, the product HuFGFR472 was obtained (0.78 g, yield: 93%).
$^1$H NMR (400 MHz, DMSO) δ 8.33 (d, J=3.0 Hz, 1H), 8.11-7.78 (m, 3H), 7.70 (dd, J=15.0, 3.0 Hz, 1H), 7.62-7.43 (m, 2H), 7.31 (d, J=15.0 Hz, 1H), 6.89 (s, 2H), 6.53 (t, J=15.0 Hz, 1H), 3.54 (s, 2H), 2.68 (dd, J=15.4, 5.2 Hz, 4H), 2.33 (dd, J=15.4, 5.4 Hz, 4H), 1.75 (s, 1H). (ESI) m/z 514 (M+1).

Example 52. Preparation of HuFGFR473

HuFGFR267 (1.0 g, 1.89 mmol) was dissolved in anhydrous methanol, and 1 M hydrogen chloride in methanol (1.89 mL) was added dropwise into the solution under ice bath condition. The reaction was carried out for 10 min at room temperature, and the solvent was evaporated to obtain HuFGFR459 (1.07 g, yield: 100%).
$^1$H NMR (400 MHz, DMSO) δ 8.33 (d, J=3.0 Hz, 1H), 8.06 (d, J=3.0 Hz, 1H), 7.97 (dd, J=15.0, 3.0 Hz, 1H), 7.88 (dd, J=15.0, 3.0 Hz, 1H), 7.70 (dd, J=15.0, 3.0 Hz, 1H), 7.61-7.51 (m, 2H), 7.31 (d, J=15.0 Hz, 1H), 6.89 (s, 2H), 6.53 (t, J=15.0 Hz, 1H), 3.54 (s, 2H), 3.14-3.03 (m, 4H), 2.89-2.82 (m, 7H). LR-MS (ESI) m/z 528 (M+1).

Example 53. Preparation of HuFGFR474

HuFGFR472 (1.0 g, 1.95 mmol) was dissolved in anhydrous DMF, potassium carbonate (0.54 g, 3.9 mmol) was successively added, and then deuterated iodomethane (0.28 g, 1.95 mmol) was added under ice bath condition. The reaction was carried out for 1 h in ice bath to obtain HuFGFR474 (0.8. g, Yield: 79%).
$^1$H NMR (400 MHz, DMSO) δ 8.33 (d, J=3.0 Hz, 1H), 8.06 (d, J=3.0 Hz, 1H), 7.97 (dd, J=15.0, 3.0 Hz, 1H), 7.88 (dd, J=15.0, 3.0 Hz, 1H), 7.79-7.46 (m, 3H), 7.31 (d, J=15.0 Hz, 1H), 6.89 (s, 2H), 6.53 (t, J=15.0 Hz, 1H), 3.54 (s, 2H), 2.61-2.42 (m, 4H), 2.40-2.20 (m, 4H). LR-MS (ESI) m/z 531 (M+1).

The structures of compound A34, HuFGFR143, HuFGFR148, HuFGFR150, HuFGFR151, Ponatinib (or AP24534) and LY2874455 are as follows:

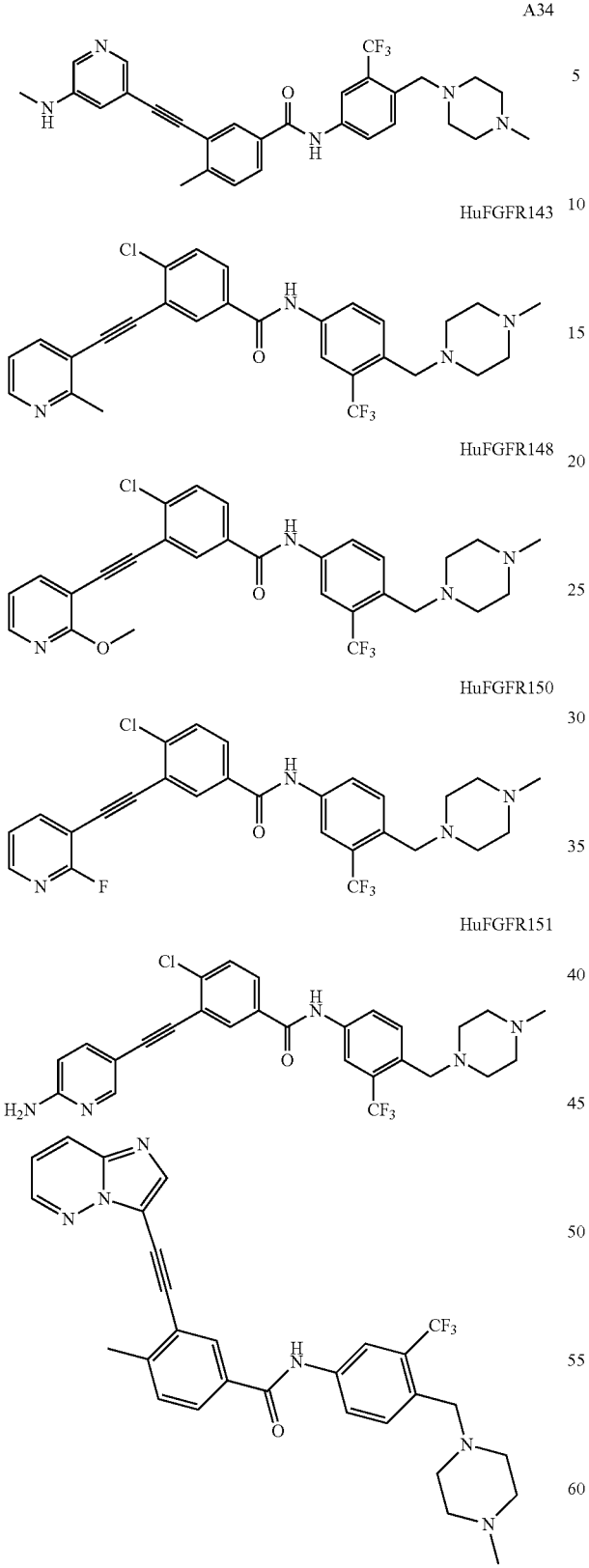

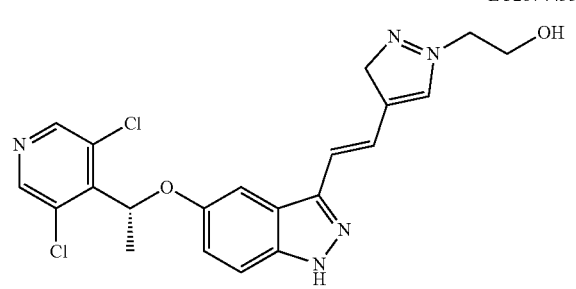

(2) Example of Biological Activity Assay

Test Example 1: Inhibition of Receptor Tyrosine Kinase Activity at Molecular Level Enzyme reaction substrate Poly(Glu, Tyr)$_{4:1}$ was diluted with potassium-free PBS (10 mM sodium phosphate buffer, 150 mM NaCl, pH 7.2-7.4) to 20 μg/mL. The enzyme label plate was coated with 125 μL/well. The reaction was conducted under 37° C. for 12-16 hours. After the liquid was removed from the wells, the plate was washed three times with 200 μL/well of T-PBS (PBS containing 0.1% Tween-20), each for 5 minutes. The enzyme plate was dried in 37° C. dryer for 1-2 hours.

50 μL ATP solution diluted with buffer (50 mM HEPES pH 7.4, 50 mM MgCl$_2$, 0.5 mM MnCl$_2$, 0.2 mM Na$_3$VO$_4$, 1 mM DTT) to a final concentration of 5 μM was added into each well. The compound was diluted with DMSO to a suitable concentration (1 μL/well) or the well contained the corresponding concentration of DMSO (negative control well) Then various kinase recombinant proteins diluted with 49 μL of reaction buffer was added to initiate the reaction. Each experiment required duplicate enzyme-free control well. The reaction was carried out for 1 hour on a 37° C. Shaker (100 rpm). The plate was washed three times with T-PBS. A dilution of the primary antibody PY99 was added (100 μL/well), and the reaction was conducted in a shaker at 37° C. for 0.5 hr. The plate was washed three times with T-PBS. A dilution of the horseradish peroxidase-labeled goat anti-mouse IgG secondary antibody was added (100 μL/well), and the reaction was conducted in a shaker at 37° C. for 0.5 hour. Plate was washed with T-PBS for three times. 2 mg/mL OPD coloration solution (diluted with 0.1 M citric acid-sodium citrate buffer containing 0.03% H$_2$O$_2$ (pH=5.4)) was added (100 μL/well), reacted for 1-10 minutes at 25° C. in dark. The reaction was quenched with 2M H$_2$SO$_4$ (50 μL/well), and read at 490 nm using a tunable microplate reader SPECTRA MAX 190.

The inhibition ratio of the sample was determined by the following formula:

$$\text{inhibition ratio of sample (\%)} = \left(1 - \frac{OD \text{ of compound well-}OD \text{ of enzyme-free control well}}{OD \text{ of negative control well-}OD \text{ of enzyme-free control well}}\right) \times 100$$

The IC$_{50}$ values were obtained via four-parameter regression analysis using the software supplied with the microplate reader.

The enzyme activity data of the compounds prepared in the present invention, compound HuFGFR151, compound HuFGFR117, the positive control Ponatinib and the positive control LY2874455 against the three enzymes of FGFR1, RET and KDR are listed in Table 1:

TABLE 1

Effect of compounds on tyrosine kinase activity

| No. | 10 nM inhibition ratio | | |
|---|---|---|---|
| | FGFR1 | RET | KDR |
| Example 1 | 77.7 | 87.6 | 45.1 |
| Example 2 | 73.0 | 69.2 | 44.3 |
| Example 3 | 52.4 | 69.1 | 34.7 |
| Example 4 | 51.1 | 52.0 | 4.6 |
| Example 5 | 45.1 | 40.1 | 15.2 |
| Example 6 | 74.7 | 57.7 | 35.2 |
| Example 7 | 80.7 | 92.4 | 38.9 |
| Example 8 | 46.0 | 53.4 | 30.4 |
| Example 9 | 60.7 | 83.4 | 28.9 |
| Example 10 | 36 | 63.4 | 34.5 |
| Example 11 | 54.0 | 68.2 | 34.3 |
| Example 12 | 75.1 | 73.2 | 24.0 |
| Example 13 | 70.2 | 64.3 | 15.1 |
| Example 14 | 46.1 | 57.6 | 20.3 |
| Example 15 | 59.9 | 61.2 | 15.4 |
| Example 16 | 70.5 | 71.8 | 25.2 |
| Example 17 | 68.0 | 73.3 | 25.0 |
| Example 18 | 65.5 | 58.2 | 20.3 |
| Example 19 | 59.3 | 69.4 | 13.2 |
| Example 20 | 71.1 | 70.8 | 23.4 |
| Example 21 | 44.3 | 58.1 | 32.0 |
| Example 22 | 75.1 | 59.3 | 24.9 |
| Example 23 | 74.1 | 60.0 | 33.1 |
| Example 24 | 64.1 | 66.1 | 23.5 |
| Example 25 | 54.5 | 49.9 | 33.2 |
| Example 26 | 77.2 | 79.4 | 24.3 |
| Example 27 | 78.2 | 69.5 | 34.1 |
| Example 28 | 68.5 | 79.3 | 28.7 |
| Example 29 | 44.9 | 55.2 | 14.3 |
| Example 30 | 55.2 | 77.8 | 5.8 |
| Example 31 | 59.3 | 67.8 | 35.1 |
| Example 32 | 66.3 | 70.8 | 37.2 |
| Example 33 | 49.8 | 77.8 | 35.1 |
| Example 34 | 44.3 | 57.8 | 18.0 |
| Example 35 | 57.9 | 44.3 | 32.1 |
| Example 36 | 49.9 | 56.3 | 12.1 |
| Example 37 | 48.1 | 66.3 | 33.2 |
| Example 38 | 51.8 | 65.3 | 44.1 |
| Example 39 | 53.4 | 88.0 | 36.4 |
| Example 40 | 58.2 | 77.3 | 36.6 |
| Example 41 | 53.4 | 77.3 | 35.4 |
| Example 42 | 52.2 | 46.5 | 18.2 |
| Example 43 | 44.1 | 55.4 | 31.2 |
| Example 44 | 49.9 | 64.3 | 21.0 |
| Example 45 | 48.6 | 69.5 | 23.8 |
| Example 46 | 48.5 | 95.1 | 43.1 |
| Example 47 | 55.1 | 89.1 | 40.8 |
| Example 48 | 48.7 | 78.0 | 34.3 |
| Example 49 | 77.1 | 69.5 | 33.2 |
| Example 50 | 56.3 | 55.1 | 27.8 |
| Example 51 | 67.9 | 79.4 | 38.2 |
| Example 52 | 75.2 | 89.3 | 40.2 |
| Example 53 | 78.3 | 87.0 | 42.1 |
| A34 | 33.2 | 16.4 | 39.5 |
| HuFGFR143 | 19.9 (100 nM) | 35.2 | 26.4 |
| HuFGFR148 | 22.4 (100 nM) | 21.7 | 18.2 |
| HuFGFR150 | 35.1 | 30.3 | 32.3 |
| HuFGFR151 | 21.1 (100 nM) | 29.7 (100 nM) | 23.9 (100 nM) |
| Ponatinib | 79.5 | 87.5 | 85.3 |
| LY2874455 | 97.5 | / | 91.6 |

Note:
Data is presented as average of inhibitory ratio of compound in two independent experiments for inhibiting kinase substrate phosphorylation.

Experimental results: As seen from Table 1, in the evaluation of biological activity, the o-aminoheteroaryl alkynyl-containing compounds of the present invention have a high activity of inhibiting FGFR1 and RET kinase at a concentration of 10 μM, while the compounds prepared in the examples of the present invention have low KDR activity. The activity of these compounds on KDR is significantly weaker than that on FGFR1 or RET, thus indicating these compounds have clear selectivity which is beneficial to solve the technical problems of hepatic toxicity and cardio-toxicity of Panatinib. Compared with the compounds of the present invention, compound HuFGFR151 has a different amino position, which results in the significant decrease of its inhibitory activity on FGFR1 and RET kinases. Compared with compound A34, HuFGFR143, HuFGFR148, and HuFGFR150, the introduction of o-amino in the compounds of the present invention results a significant increase in the activity against FGFR1 and RET kinases and selectivity. However, the KDR activity of the positive control drugs (Ponatinib and LY2874455) is high.

The inhibitory activity data of the compounds HuFGFR267 and HuFGFR293 against the RET-related mutant enzyme are shown in Table 2, wherein, Ret (V804M) is a commercially available recombinant protein. The results showed that HuFGFR267 and HuFGFR293 had significant inhibitory activities against Ret and Ret (V804M), especially for Ret and its V804M mutant kinase.

TABLE 2

$IC_{50}$ value for compounds against tyrosine kinase activity (nM)

| Kinase | $IC_{50}$ (nM) | |
|---|---|---|
| | HuFGFR267 | HuFGFR293 |
| Ret | 1.4 ± 0.6 | 6.0 ± 0.4 |
| Ret (V804M) | 8.4 ± 1.7 | 17.9 ± 5.4 |

Note:
The inhibitory $IC_{50}$ value of compounds on phosphorylation of kinase substrate was independently measured twice and presented as Mean ± SD.

Pharmacological Experiment 2: Receptor Tyrosine Kinase-Dependent Inhibition Assay at Cellular Level Detecting the Effect of Compounds on the Activation of RET Signaling Pathway in TT and BaF3/CCDC6-RET Cells by Western Blotting The cells were seeded into a 12-well plate (250,000/well). After incubation for 18-24 hours, the compounds were added to react for 2 hours, and then the cells were collected and firstly washed once with cold PBS (containing 1 mmol sodium vanadate); then 1×SDS gel loading buffer (50 mmol Tris-HCl (pH 6.8), 100 mmol DTT, 2% SDS, 10% glycerol, 1 mmol sodium vanadate, 0.1% bromophenol blue) was added to lyse cells. The cell lysate was heated in a boiling water bath for 10 minutes, and then centrifuged at 12,000 rpm for 10 minutes at 4° C.

The supernatant was taken for SDS-PAGE electrophoresis (Mini-PROTEAN 3 Cell, Bio-Rad, Hercules, Calif., USA). After electrophoresis, the proteins were transferred to a nitrocellulose membrane using a semi-dry electrotransfer system (Amersham Life Sciences, Arlington Heights, Ill., USA). The nitrocellulose membrane was placed in a blocking solution (5% skim milk powder diluted in TBS containing 1 mmol sodium vanadate) for 2 hours at room temperature, and then the membrane was placed and reacted with a primary antibody at 4° C. overnight. The membrane was washed three times with TBS containing 1 mmol sodium vanadate for 15 min each time. The membrane was placed in a secondary antibody solution and reacted for 1-2 hours at room temperature. After the membrane was washed three times as above, the membrane was stained using ECL (Picece, Rockford, Ill.) reagent was used for staining and then developed.

The results that Compound HuFGFR267 (267), HuFGFR293 (293) and positive control Ponatinib inhibited RET phosphorylation and the downstream signaling pathway in tumor cells and tool cell lines were shown in FIG. 1. As seen from FIG. 1, the o-aminoheteroaryl alkynyl-containing compound of the present invention targeted to and significantly inhibited the activation of the RET signaling pathway at the cellular level.

The AZD4547 structure is as follows:

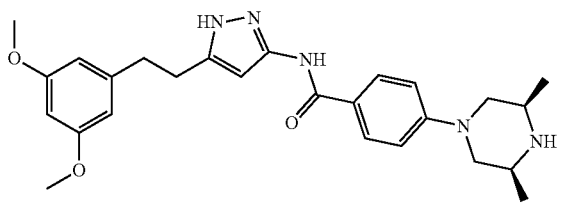 [SMILES: COc1cc(CCc2cc(NC(=O)c3ccc(N4C[C@@H](C)N[C@@H](C)C4)cc3)n[nH]2)cc(OC)c1]

Pharmacological Experiment 3: Evaluation of the Inhibitory Effect of Compounds on Growth of Subcutaneous Xenografts of Human Lung Cancer NCI-H1581 and Human Gastric Cancer SNU-16 in Nude Mice 1. Inhibition Activity of Compound HuFGFR267 on Growth of Subcutaneous Xenografts of Human Lung Cancer NCI-H1581 and Human Gastric Cancer SNU-16 in Nude Mice The tumor tissue in the vigorous growth period was cut into about 1.5 mm$^3$, and inoculated subcutaneously in the right axilla of nude mice under aseptic conditions. The diameter of the subcutaneously implanted tumor in nude mice was measured by a vernier caliper. The animals were randomly divided into groups when the average volume was about 120 mm$^3$. In the compound HuFGFR267 50 mg/kg group, the compound was formulated with 0.5% methylcellulose (MC) to the required concentration before use. The formulation of compound was prepared once a week, and orally administered once a day for 14 days. The positive control drug AZD4547 was diluted to the required concentration with water for injection containing 1% Tween 80 before use. The formulation of AZD4547 was prepared once a week, and orally administered once a day for 14 days. In the solvent control group, an equal amount of water for injection was administrated. The diameter of the transplanted tumor was measured twice a week during the entire experiment, and the body weight of the mice was weighed. The tumor volume (TV) was calculated as: TV=½×a×b$^2$, where a and b represented length and width, respectively. The relative tumor volume (RTV) was calculated based on the measured results, and the formula was: RTV=V$_t$/V$_0$, wherein V$_0$ represented the tumor volume obtained when the mice was divided and administered (i.e., d$_0$), and V$_t$ represented the tumor volume at each measurement. The evaluation index of antitumor activity was: relative tumor proliferation rate T/C (%), and the formula was as follows: T/C (%)=(T$_{RTV}$/C$_{RTV}$)×100%, wherein T$_{RTV}$ was TRV in treatment group; and C$_{RTV}$ was RTV in negative control group.

The results of the inhibitory effect of the compound HuFGFR267 on growth of xenografts of human lung cancer NCI-H1581 in nude mice are shown in Table 3 and FIG. 2, wherein the data in Table 3 correspond to numerical points in the curve of FIG. 2. As seen from FIG. 2, in HuFGFR267 50 mg/kg group, after orally administered once a day for 14 days, the growth of subcutaneously xenografts of human lung cancer NCI-H1581 in nude mice was significantly inhibited, and T/C obtained on the 14th day was 3.77%. In the positive control AZD4547 12.5 mg/kg group, it was administrated in the same way as above, and the growth of subcutaneously xenografts of human lung cancer NCI-H1581 in nude mice was significantly inhibited and the T/C obtained on the 14th day was 24.03%. During the experiment, no mice died, and the mice in each group were in good condition. It can be seen from FIG. 3 and Table 4 (wherein the data in Table 4 correspond to numerical points in the curve of FIG. 3), the body weight of mice bearing human lung cancer NCI-H1581 tumor in the compound HuFGFR267 group had no significant change. Thus, it indicated that the o-aminoheteroaryl alkynyl-containing compound of the present invention had a significant inhibitory effect on the growth of subcutaneous xenografts of human lung cancer NCI-H1581 in nude mice, and advantage of low toxicity.

TABLE 3

Effect of HuFGFR-267 on tumor volume of xenografts of human lung cancer NCI-H1581 in nude mice

| Group | Relative tumor volume RTV (mean ± SD) | | | | |
| --- | --- | --- | --- | --- | --- |
| | d0 | d3 | d7 | d10 | d14 |
| Solvent control | 1.00 ± 0.00 | 3.38 ± 1.59 | 15.26 ± 4.04 | 28.78 ± 7.04 | 57.48 ± 35.29 |
| AZD4547 12.5 mg/kg | 1.00 ± 0.00 | 1.27 ± 0.44 | 3.43 ± 1.14 | 5.57 ± 3.62 | 13.81 ± 4.56 |
| | P value | 0.0061 | 0.0000 | 0.0000 | 0.0090 |
| HuFGFR-267 50 mg/kg | 1.00 ± 0.00 | 1.28 ± 0.40 | 1.33 ± 0.74 | 2.02 ± 1.10 | 2.16 ± 1.41 |
| | P value | 0.0062 | 0.0000 | 0.0000 | 0.0016 |

Note:
P value is vs solvent control

TABLE 4

Effect of HuFGFR-267 on body weight of mice bearing human lung cancer NCI-H1581 tumor

| Group | Weight (g, mean ± SD) | | | | |
|---|---|---|---|---|---|
| | d0 | d3 | d7 | d10 | d14 |
| Solvent control | 18.2 ± 1.5 | 9.0 ± 1.8 | 20.9 ± 2.0 | 22.2 ± 2.8 | 24.2 ± 3.2 |
| AZD4547 12.5 mg/kg | 18.2 ± 1.6 | 19.3 ± 1.6 | 20.1 ± 1.9 | 20.6 ± 2.2 | 21.3 ± 2.3 |
| HuFGFR-267 50 mg/kg | 18.1 ± 1.2 | 19.2 ± 1.0 | 19.7 ± 1.0 | 20.2 ± 1.2 | 20.0 ± 1.3 |

Figure 5:
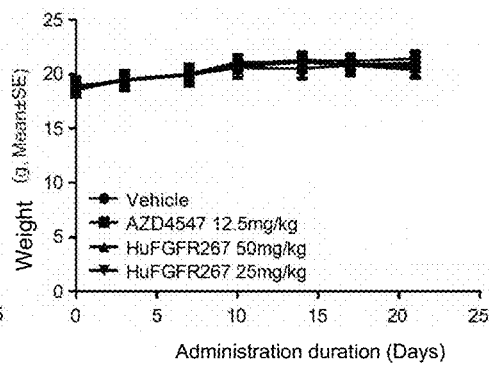
FIG. 5 is a line diagram of the pharmacological experiment example 3 which shows that the effects of the compounds HuFGFR267 and AZD4547 on the body weight of mice bearing human gastric cancer SNU-16 tumor.

The results of the inhibitory effect of compound HuFGFR267 on growth of human gastric cancer SNU-16 xenografts in nude mice are shown in FIG. 4, wherein the data of Table 5 correspond to numerical points in the curve of FIG. 4. In HuFGFR267 50 mg/kg and 25 mg/kg groups, compounds were administered orally once a day for 21 days, and the growth of human gastric cancer SNU-16 xenografts in nude mice was which significantly inhibited. The T/C values obtained on day 21 were 11.66% and 18.55%, respectively. In the positive control AZD4547 12.5 mg/kg group, AZD4547 was administered in the same way as above and the growth of subcutaneous xenografts of human gastric cancer SNU-16 in nude mice was significantly inhibited. T/C obtained on day 21 was 18.46%. During the experiment, no mice died, and the mice in each group were in good condition. As seen from FIG. 5 (the data in Table 6 correspond to each numerical points in the curve of FIG. 5), body weight of mice bearing human gastric cancer SNU-16 tumor in the compound HuFGFR267 group had no significant change. Thus, it indicated that the o-aminoheteroaryl alkynyl-containing compound of the present invention had a significant inhibitory effect on the growth of subcutaneous xenografts of human gastric cancer SNU-16 in nude mice, and advantage of low toxicity.

2. Inhibitory Effects of the Comparative Compounds HuFGFR1-117 and HuFGFR1-113 (Structure are Shown Below) on Growth of Subcutaneous Xenografts of Human Gastric Cancer SNU-16 in Nude Mice

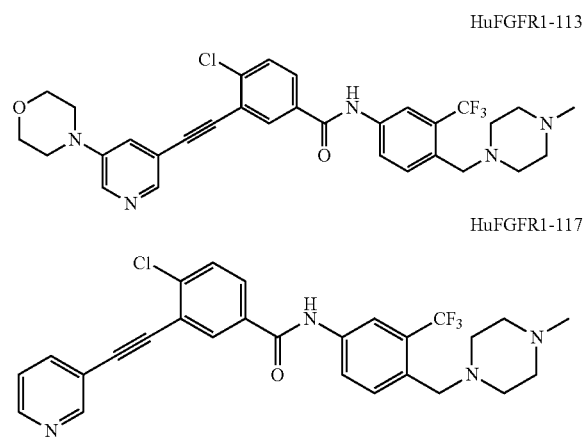

HuFGFR1-113

HuFGFR1-117

TABLE 5

Effect of HuFGFR-267 on tumor volume of xenografts of human gastric cancer SNU-16 in nude mice.

| Group | Relative tumor volume RTV (mean ± SD) | | | | | | |
|---|---|---|---|---|---|---|---|
| | 2016 Dec. 20 d0 | 2016 Dec. 23 d3 | 2016 Dec. 27 d7 | 2016 Dec. 30 d10 | 2017 Jan. 3 d14 | 2017 Jan. 6 d17 | 2017 Jan. 10 d21 |
| Solvent control | 1.00 ± 0.00 | 2.86 ± 2.01 | 7.2 ± 2.86 | 10.03 ± 4.29 | 14.79 ± 7.10 | 18.72 ± 8.50 | 23.44 ± 9.95 |
| AZD4547 12.5 mg/kg | 1.00 ± 0.00 | 0.92 ± 0.29 | 2.34 ± 1.23 | 2.96 ± 2.19 | 3.36 ± 3.14 | 3.77 ± 2.56 | 4.33 ± 3.29 |
| P value | | 0.0338 | 0.0012 | 0.0017 | 0.0018 | 0.0007 | 0.0003 |
| HuFGFR-267 50 mg/kg | 1.00 ± 0.00 | 1.11 ± 0.42 | 0.83 ± 0.49 | 1.26 ± 0.71 | 1.89 ± 1.57 | 2.02 ± 1.63 | 2.73 ± 2.82 |
| P value | | 0.0537 | 0.0001 | 0.0002 | 0.0005 | 0.0002 | 0.0002 |
| HuFGFR-267 25 mg/kg | 1.00 ± 0.00 | 1.74 ± 0.58 | 2.51 ± 0.93 | 3.13 ± 1.51 | 3.79 ± 1.93 | 3.97 ± 1.58 | 4.35 ± 2.03 |
| P value | | 0.2038 | 0.0014 | 0.0016 | 0.0020 | 0.0008 | 0.0003 |

TABLE 6

Effect of HuFGFR-267 on body weight of mice bearing human gastric cancer SNU-16 tumor

| Group | Weight (g, mean ± SD) | | | | | | |
|---|---|---|---|---|---|---|---|
| | 2016 Dec. 20 d0 | 2016 Dec. 23 d3 | 2016 Dec. 27 d7 | 2016 Dec. 30 d10 | 2017 Jan. 3 d14 | 2017 Jan. 6 d17 | 2017 Jan. 10 d21 |
| Solvent control | 18.5 ± 1.3 | 19.5 ± 1.4 | 20.0 ± 1.9 | 21.1 ± 2.2 | 21.1 ± 2.4 | 20.8 ± 2.5 | 20.4 ± 2.5 |
| AZD4547 12.5 mg/kg | 18.8 ± 1.2 | 19.5 ± 1.3 | 20.0 ± 1.5 | 20.7 ± 1.5 | 21.1 ± 1.6 | 20.9 ± 1.7 | 21.0 ± 1.7 |
| HuFGFR-267 50 mg/kg | 18.9 ± 1.9 | 19.4 ± 2.2 | 19.9 ± 2.4 | 20.6 ± 2.3 | 20.5 ± 2.2 | 20.8 ± 2.3 | 20.7 ± 2.2 |
| HuFGFR-267 25 mg/kg | 18.6 ± 1.6 | 19.4 ± 1.7 | 20.0 ± 1.8 | 20.9 ± 1.8 | 21.3 ± 1.7 | 21.2 ± 1.6 | 21.4 ± 1.8 |

The tumor tissue in the vigorous growth period was cut into 1.5 mm³, and inoculated subcutaneously in the right axilla of nude mice under aseptic conditions. The diameter of the xenograft in nude mice was measured with a vernier caliper. The animals were randomly divided into groups when the average tumor volume was grown to about 190 mm³. In HuFGFR1-113 and HuFGFR1-117 groups (100 mg/kg and 20 mg/kg) the compounds were orally administered once a day for 21 consecutive days. In the positive control drug Ponatinib 30 mg/kg group, Ponatinib was orally administered once a day for 21 days. In the solvent control group, mice were gave an equal amount of solvent. The diameter of the xenograft was measured twice a week during the entire experiment, and the body weight of the mice was weighed. The tumor volume (TV) was calculated as: TV=½×a×b², where a and b represented length and width, respectively. The relative tumor volume (RTV) was calculated based on the measured results, and the formula was: $RTV=V_t/V_0$, wherein $V_0$ represented the tumor volume obtained when the mice was divided and administered (i.e., $d_0$), and $V_t$ represented the tumor volume at each measurement. The anti-tumor activity evaluation index was the relative tumor proliferation rate T/C (%), and the calculation formula was as follows: T/C (%)=$(T_{RTV}/C_{RTV})\times100\%$, wherein $T_{RTV}$ was TRV in treatment group; and $C_{RTV}$ was RTV in negative control group.

Figure 6:
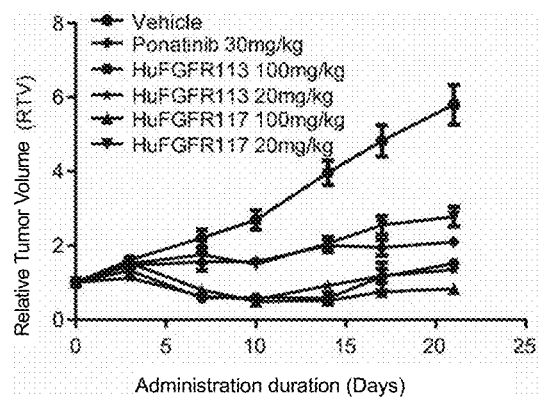
FIG. 6 is a line diagram of the pharmacological experiment example 3 which shows the inhibitory effect of the comparative compounds HuFGFR1-117 and HuFGFR1-113 on growth of subcutaneous human gastric cancer SNU-16 xenografts in nude mice.
Figure 7:
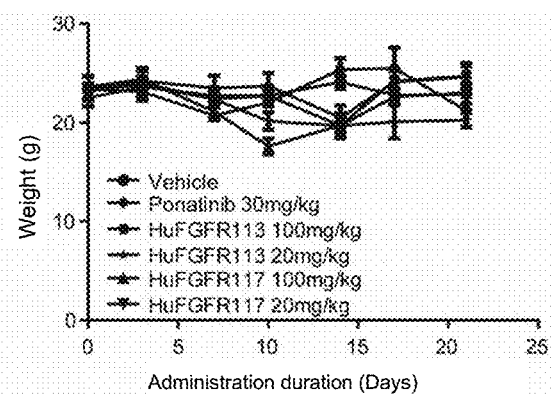
FIG. 7 is a line diagram of the pharmacological experiment example 3 which shows that the effect of the comparative compounds HuFGFR1-117 and HuFGFR1-113 on the body weight of mice bearing human gastric cancer SNU-16 tumor.

The experimental results are shown in FIGS. 6 and 7 (where the data in Tables 7 and 8 correspond to the numerical values in the curves of FIGS. 6 and 7, respectively). HuFGFR1-113 100 mg/kg group showed significant toxicity, and administration was stopped due to the mice were found to have a poor state with low temperature on the second day. One mouse died on the third day. Two mice died on the fifth day. The compound was administrated again because the mouse was recovered on day 20. In HuFGFR1-113 20 mg/kg group, the compound was administered orally once a day for 21 days, and the growth of human gastric cancer SNU-16 in nude mice was significantly inhibited. The T/C obtained on day 21 was 23.30%, but one mouse died on day 20. In the compound HuFGFR1-117 100 mg/kg group, the growth of subcutaneous xenograft of human gastric cancer SNU-16 in nude mice was significantly inhibited. The T/C obtained on day 21 was 14.38%, but one mouse died on the 9th and 10th day respectively, and other mice showed dry skin, molting, and poor condition, so the administration was stopped. The administration was started again because the mice was recovered and the molting disappeared and the skin returned to normal on day 17. In HuFGFR1-117 20 mg/kg group, it was orally administered once a day, and the growth of subcutaneous xenografts of human gastric cancer SNU-16 in nude mice was weakly inhibited. The T/C obtained on day 21 was 47.88%, and the tumor inhibition rate was low. In the Ponatinib 30 mg/kg group, it was orally administered once a day for 21 days, and the growth of subcutaneous xenografts of human gastric cancer SNU-16 in nude mice was significantly inhibited. The T/C obtained on day 21 was 36.20%.

TABLE 7

Effect of various compounds on tumor volume of xenografts of human gastric cancer SNU-16 in nude mice

| Group | | d0 | d3 | d7 | d10 | d14 | d17 | d21 |
|---|---|---|---|---|---|---|---|---|
| Solvent control | | 1.00 ± 0.00 | 1.61 ± 0.40 | 2.20 ± 0.70 | 2.69 ± 0.81 | 3.96 ± 1.03 | 4.82 ± 1.34 | 5.80 ± 1.66 |
| Ponatinib 30 mg/kg | | 1.00 ± 0.00 | 1.46 ± 0.30 | 1.56 ± 0.52 | 1.56 ± 0.22 | 2.00 ± 0.38 | 1.94 ± 0.47 | 2.10 ± 0.34 |
| | P value | 0.4763 | 0.0942 | 0.0099 | 0.0013 | 0.0005 | 0.0003 | |
| HuFGFR1-113 100 mg/kg | | 1.00 ± 0.00 | 1.32 ± 0.40 | 0.58 ± 0.02 | 0.60 ± 0.02 | 0.58 ± 0.35 | 1.16 ± 0.86 | 1.52 ± / |
| | P value | 0.2142 | 0.0106 | 0.0055 | 0.0012 | 0.0045 | | / |
| HuFGFR1-113 20 mg/kg | | 1.00 ± 0.00 | 1.12 ± 0.03 | 0.64 ± 0.23 | 0.54 ± 0.22 | 0.92 ± 0.17 | 1.18 ± 0.42 | 1.35 ± 0.15 |
| | P value | 0.0200 | 0.0004 | 0.0001 | 0.0000 | 0.0001 | 0.0002 | |
| HuFGFR1-117 100 mg/kg | | 1.00 ± 0.00 | 1.53 ± 0.39 | 0.80 ± 0.18 | 0.49 ± 0.08 | 0.51 ± 0.19 | 0.75 ± 0.22 | 0.83 ± 0.31 |
| | P value | 0.7229 | 0.0008 | 0.0008 | 0.0002 | 0.0004 | 0.0004 | |
| HuFGFR1-117 20 mg/kg | | 1.00 ± 0.00 | 1.51 ± 0.37 | 1.75 ± 0.47 | 1.49 ± 0.14 | 2.06 ± 0.38 | 2.55 ± 0.55 | 2.78 ± 0.58 |
| | P value | 0.6558 | 0.2154 | 0.0065 | 0.0017 | 0.0033 | 0.0019 | |

Note:
P value is vs solvent control

TABLE 8

Effect of various compounds on body weight of mice bearing human gastric cancer SNU-16 tumor

| Group | 2014 Apr. 28 d0 | 2014 May 1 d3 | 2014 May 5 d7 | 2014 May 8 d10 | 2014 May 12 d14 | 2014 May 15 d17 | 2014 May 19 d21 |
|---|---|---|---|---|---|---|---|
| Solvent control | 23.4 ± 1.5 | 23.8 ± 1.4 | 22.4 ± 1.7 | 22.7 ± 1.9 | 24.1 ± 2.1 | 22.8 ± 2.4 | 22.9 ± 2.8 |
| Ponatinib 30 mg/kg | 23.6 ± 2.5 | 24.2 ± 2.9 | 23.5 ± 2.8 | 23.7 ± 2.9 | 24.5 ± 2.8 | 24.1 ± 2.6 | 24.6 ± 3.1 |
| HuFGFR1-113 100 mg/kg | 23.4 ± 2.7 | 23.1 ± 2.0 | 20.7 ± 0.1 | 22.1 ± 0.4 | 25.4 ± 1.6 | 25.5 ± 3.0 | 21.2 ± / |
| HuFGFR1-113 20 mg/kg | 23.2 ± 1.8 | 24.0 ± 1.5 | 22.4 ± 1.8 | 20.2 ± 1.9 | 19.7 ± 2.9 | 20.1 ± 3.7 | 20.3 ± 1.6 |
| HuFGFR1-117 100 mg/kg | 23.6 ± 0.7 | 24.4 ± 1.8 | 21.1 ± 1.9 | 17.6 ± 1.8 | 19.7 ± 2.0 | 22.6 ± 1.5 | 23.0 ± 2.4 |
| HuFGFR1-117 20 mg/kg | 22.5 ± 1.9 | 23.6 ± 2.1 | 22.7 ± 2.0 | 22.7 ± 2.3 | 23.6 ± 2.4 | 24.2 ± 2.5 | 24.7 ± 2.3 |

Experimental conclusion: The HuFGFR267 of the present invention significantly inhibited the growth of subcutaneous xenografts of human gastric cancer SNU-16 in nude mice, and the T/C obtained on day 21 was 11.66% and 18.55%, respectively. The weight of the tumor-bearing mice did not change significantly and the mice were in good condition. Compound HuFGFR1-113 (morpholine substituted in meta-position of pyridine) which was structurally similar to compound HuFGFR267 of the present invention, had a weaker inhibition on growth of subcutaneous xenografts of human gastric cancer SNU-16 in nude mice at the dosage of 20 mg/kg than that of HuFGFR267, and the T/C obtained on day 21 was 23.30%, while the weight of the tumor-bearing mice decreased significantly. One mouse died on day 20. The dosage of 100 mg/kg showed great toxicity. The mice were found to have poor state with low temperature on the second day. One mouse died on the third day. Two mice died on the fifth day. Another compound HuFGFR1-117 (without amino substitution in the o-position of pyridine) which was structurally similar to HuFGFR267 of the present invention, has a weaker inhibitory effect on the growth of subcutaneous xenografts of human gastric cancer SNU-16 in nude mice than that of HuFGFR267, and T/C obtained on day 21 were 14.38% and 47.88%, while the weight of the tumor-bearing mice was significantly decreased. One mouse died on the 9th and 10th day respectively, and other mice appeared dry skin, molting and poor state. It indicates that the introduction of the o-amino of the pyridine in the present invention can effectively increase the tumor inhibitory activity of compounds and exhibit a significant advantage of low toxicity.

Experimental Example 4: Pharmacokinetic Experiment in Rat

Ponatinib (AP24534) was administered intravenously (IV) and orally (PO) to SD rats. Blood samples were taken at different time points. LC-MS/MS was used to determine the concentration of compound in the plasma of rats after administration of the test compound, and the relevant pharmacokinetic parameters were calculated to examine oral bioavailability and pharmacokinetic properties of the compound in rats. The results are shown in Table 3.

TABLE 3

| Administration route | $CL_{plasma}$ (mL/kg/min) | $Vd_{ss}$ (L/kg) | $T_{max}$ (h) | $T_{1/2}$ (h) | $C_{max}$ (ng/mL) | $AUC_{0-t}$ (ng * h/mL) | F |
|---|---|---|---|---|---|---|---|
| IV (2 mg/kg) | 22.2 | 7.78 | — | 4.24 | — | 1413 | — |
| PO (10 mg/kg) | — | — | 2.33 | 8.29 | 241 | 1603 | 24.4% |

Compound HuFGFR267 was administered intravenously and orally to SD rats. Blood samples were taken at different time points. LC-MS/MS was used to determine the concentration of compound in the plasma of rats after administration of the test compound, and the relevant pharmacokinetic parameters were calculated to examine oral bioavailability and pharmacokinetic properties of the compound in rats. The results are shown in Table 4.

TABLE 4

| Administration route | $CL_{plasma}$ (mL/kg/min) | $Vd_{ss}$ (L/kg) | $T_{max}$ (h) | $T_{1/2}$ (h) | $C_{max}$ (ng/mL) | $AUC_{0-t}$ (ng * h/mL) | F |
|---|---|---|---|---|---|---|---|
| IV (2 mg/kg) | 11.9 | 4.88 | — | 6.00 | — | 2720 | — |
| PO (10 mg/kg) | — | — | 5.33 | 10.5 | 346 | 4961 | 36.5% |

It can be seen from Table 3 and Table 4 that compound HuFGFR267 is superior to the marketed drug AP24534 in the aspect of exposure, thus having a better potential for developing into a medicine.

In summary, the o-aminoheteroaryl alkynyl-containing compounds in the examples of the present invention have advantages of a high FGFR and RET dual-targeting inhibitory activity and a relatively low KDR activity. The compound of formula (I) exhibits a strong inhibitory activity on human lung cancer cell line NCI-H1581 and gastric cancer cell line SNU16 as well as an RET-dependent sensitive cell line BaF3-CCDC6-Ret and mutants thereof. Pharmacokinetic data has shown that the o-aminoheteroaryl alkynyl-containing compound has good druggability, and exhibits significant inhibition on the growth of related tumors in a long-term animal model while in the efficacy dosage, the animal has a good condition (including no significant decrease in body weight), and no significant toxicity is observed (no animal death or molting).

The preferred embodiments of the present invention have been described above in detail in combination with the attached drawings. However, the present invention is not limited to the specific details of the embodiments described above. Various simple modifications can be made to the technical solutions of the present invention within the scope of the technical conception of the present invention and such simple modifications fall into the scope of the present invention.

The invention claimed is:

1. A compound of formula (I), or a deuterated compound, or a pharmaceutically acceptable salt or a prodrug thereof:

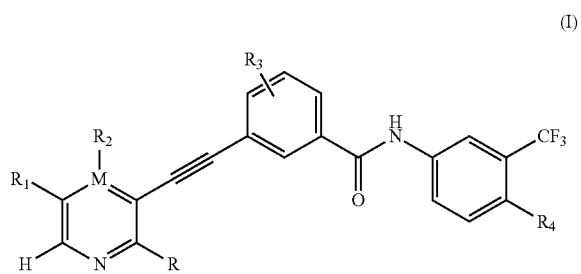

(I)

wherein:

R is amino which is optionally substituted with one or more alkyl or modified alkyl;

M is C or N, and when M is N, $R_2$ is none;

$R_1$ is selected from —H, —N($Q_1$)($Q_2$), amino, halogen, hydroxyl, cyano, aryl, heteroaryl, alkyl or modified alkyl;

$R_2$ is selected from —H, —N($Q_1$)($Q_2$), amino, halogen, hydroxyl, oxo, aryl, heteroaryl, alkyl or modified alkyl;

$R_3$ is selected from —H, halogen, cyano, alkyl or modified alkyl;

$R_4$ is selected from —(CH$_2$)$_n$N($R_7$)($R_8$), —NHR$_9$, —OR$_9$ or modified alkyl;

$R_7$ and $R_8$ together with the adjacent N atom form a heteroaryl ring;

$R_9$ is selected from —H, aryl or heteroaryl;

each of $Q_1$ and $Q_2$ is independently selected from —H, aryl, alkyl or modified alkyl, and at least one of $Q_1$ and $Q_2$ is an aryl;

each of the aryl, heteroaryl, heteroaryl ring is independently and optionally substituted by one or more substituents selected from the group consisting of halogen, oxo, alkyl and modified alkyl;

the alkyl is a saturated aliphatic straight or branched alkyl group having 1-6 carbon atoms;

the modified alkyl is an alkyl having 1-6 carbon atoms in which any carbon (primary, secondary, tertiary or quaternary carbon group) is substituted with one or more substituents selected from —O—, —OH, —(C═O)—, halogen, primary amino, secondary amino, tertiary amino, cycloalkyl, cycloalkylene, heterocyclyl, and heterocyclylene, and a carbon-carbon single bond of the alkyl are optionally and independently replaced by a carbon-carbon double bond or a carbon-carbon triple bond;

the halogen is each independently selected from the group consisting of F, Cl, Br, and I;

the aryl is a 5-10-membered monocyclic or fused bicyclic ring;

the heteroaryl or heteroaryl ring is a 5-10 membered aromatic monocyclic or fused bicyclic ring having one or more heteroatoms selected from N, O, and S;

the cycloalkyl is a saturated or unsaturated 3-10 membered monocyclic or polycyclic alicyclic ring;

the cycloalkylene is a saturated or unsaturated 3-10 membered monocyclic or polycyclic aliphatic cycloalkylene;

the heterocyclyl is a saturated or unsaturated 3-10 membered monocyclic or polycyclic aliphatic heterocycle containing one or more heteroatoms selected from N, O, and S;

the heterocyclylene is a saturated or unsaturated 3-10 membered monocyclic or polycyclic aliphatic heterocyclylene containing one or more heteroatoms selected from N, O, and S;

n is 0-3.

2. The compound, or the deuterated compound, or the pharmaceutically acceptable salt or the prodrug thereof of claim 1, wherein:

the alkyl is a saturated aliphatic straight or branched alkyl having 1 to 6 carbon atoms;

the modified alkyl is an alkyl having one or more substituents selected from the group consisting of —O—, —COO—, —CONH—, —CH═CH—, —C≡C—, halogen, hydroxyl, carboxyl, primary amino, secondary amino, tertiary amino, cycloalkyl, heterocyclyl, and heterocyclylene;

the aryl is a 6-10 membered monocyclic or fused bicyclic ring;

the heteroaryl or heteroaryl ring is a 6-10 membered monocyclic or fused bicyclic ring containing 1-3 heteroatoms selected from N, O and S;

the cycloalkyl is a saturated or unsaturated 3-6 membered monocyclic or polycyclic ring;

the cycloalkylene is a saturated or unsaturated 3-6 membered monocyclic or polycyclic ring;

the heterocyclyl is a 4-7 membered monocyclic or polycyclic heterocycle containing 1-3 heteroatoms selected from N, O, and S;

the heterocyclylene is a 4-7 membered monocyclic or polycyclic heterocycle containing 1-3 heteroatoms selected from N, O, and S; n is 0 to 1.

3. The compound, or the deuterated compound, or the pharmaceutically acceptable salt or prodrug thereof of claim 1, wherein:

R is amino;

M is C or N, and when M is N, $R_2$ is none;

$R_1$ is selected from: —H, —N($Q_1$)($Q_2$), —N($Q_1$')($Q_2$'), halogen, hydroxyl, cyano, $C_1$-$C_6$ alkyl (optionally substituted by 1 to 5 halogens), amino $C_1$-$C_6$ alkyl, methylamino $C_1$-$C_6$ alkyl, dimethylamino $C_1$-$C_6$ alkyl, $C_1$-$C_6$ alkoxyl, hydroxyl $C_1$-$C_6$ alkyl, $C_3$-$C_6$ cycloalkyl, carboxyl, —C(═O)O($C_1$-$C_6$ alkyl), —C(═O)NH($C_1$-$C_6$ alkyl), $C_6$-$C_{10}$ aryl, 5-8 membered heteroaryl or 4-7 membered heterocyclyl;

$R_2$ is selected from —H, —N($Q_1$)($Q_2$), —N($Q_1$')($Q_2$'), halogen, hydroxyl, oxo, $C_1$-$C_6$ alkyl (optionally substituted by 1-5 halogens), amino $C_1$-$C_6$ alkyl, methylamino $C_1$-$C_6$ alkyl, dimethylamino $C_1$-$C_6$ alkyl, $C_1$-$C_6$ alkoxy, hydroxyl $C_1$-$C_6$ alkyl, $C_3$-$C_6$ cycloalkyl, $C_6$-$C_{10}$ aryl, 5-8 membered heteroaryl or 4-7 membered heterocyclyl;

each of $Q_1$ and $Q_2$ is independently selected from —H, $C_1$-$C_6$ alkyl, $C_3$-$C_6$ cycloalkyl, $C_1$-$C_6$ alkanoyl, $C_1$-$C_6$ enoyl or phenyl, and at least one of $Q_1$ or $Q_2$ is phenyl, wherein the phenyl is optionally substituted by one or more substituents selected from the group consisting of halogen, $C_1$-$C_6$ alkyl, $C_1$-$C_6$ haloalkyl, and $C_1$-$C_6$ alkoxyl;

each of $Q_1$' and $Q_2$' is independently selected from the group consisting of —H, $C_1$-$C_6$ alkyl, $C_3$-$C_6$ cycloalkyl, $C_1$-$C_6$ alkanoyl and $C_1$-$C_6$ enoyl;

$R_3$ is selected from —H, halogen, cyano, an optionally halogenated $C_1$-$C_6$ alkyl, $C_1$-$C_6$ alkoxy or $C_3$-$C_6$ cycloalkyl;

$R_4$ is selected from —(CH$_2$)nN($R_7$')($R_8$'), —NHR$_9$' or —OR$_9$';

wherein n is 0 or 1;

$R_7$' and $R_8$' are each independently selected from —H, an optionally halogenated $C_1$-$C_6$ alkyl, $C_3$-$C_6$ cycloalkyl; or $R_7$' and $R_8$' together with the adjacent N atom form a 5-10 membered heteroaryl ring or a 4-10 membered heterocycle;

$R_9$' is selected from $C_6$-$C_{10}$ aryl, 5-10 membered heteroaryl, or 4-7 membered heterocyclyl;

the $C_6$-$C_{10}$ aryl, 5-10 membered heteroaryl, 4-7 membered heterocyclyl, 5-10 membered heteroaryl ring, and 4-10 membered heterocycle are optionally and independently substituted by one or more substituents selected from the group consisting of halogen, oxo, $C_1$-$C_6$ alkyl, $C_1$-$C_6$ haloalkyl, and $C_1$-$C_6$ alkoxy;

each of the 5-10 membered heteroaryl, the 4-7 membered heterocyclyl, the 5-10 membered heteroaryl ring, and the 4-10 membered heterocycle independently contains 1-3 heteroatoms selected from N, O, and S.

4. The compound, or the deuterated compound, or the pharmaceutically acceptable salt or the prodrug thereof of claim 1, wherein:

M is C or N, and when M is N, $R_2$ is none;

$R_1$ is selected from —H, —N($Q_1$)($Q_2$), —N($Q_1$')($Q_2$'), $C_1$-$C_4$ alkyl (optionally substituted with 1-3 halogens), amino $C_1$-$C_4$ alkyl, methylamino $C_1$-$C_4$ alkyl, dimethylamino $C_1$-$C_4$ alkyl, $C_1$-$C_4$ alkoxy, hydroxy $C_1$-$C_4$ alkyl, $C_3$-$C_6$ cycloalkyl, carboxyl, —C(=O)O($C_1$-$C_4$ alkyl), —C(=O)NH($C_1$-$C_4$ alkyl), $C_6$-$C_{10}$ aryl, 5-6 membered heteroaryl or 4-6 membered heterocyclyl;

$R_2$ is selected from —H, halogen, hydroxy, oxo, $C_1$-$C_4$ alkyl (optionally substituted with 1-3 halogens), amino $C_1$-$C_4$ alkyl, methylamino $C_1$-$C_4$ alkyl, dimethylamino $C_1$-$C_4$ alkyl, $C_1$-$C_4$ alkoxy, hydroxy $C_1$-$C_4$ alkyl, $C_3$-$C_6$ cycloalkyl, $C_6$-$C_{10}$ aryl, 5-6 membered heteroaryl or 4-6 membered heterocyclic;

each of $Q_1$ and $Q_2$ is each independently selected from —H, $C_1$-$C_4$ alkyl, $C_3$-$C_6$ cycloalkyl, $C_1$-$C_4$ alkanoyl, $C_1$-$C_4$ enoyl or phenyl, and at least one of $Q_1$ and $Q_2$ is phenyl, wherein the phenyl is optionally substituted with one or more substituents selected from the group consisting of halogen, $C_1$-$C_4$ alkyl, $C_1$-$C_4$ haloalkyl, and $C_1$-$C_4$ alkoxy;

each of $Q_1'$ and $Q_2'$ is independently selected from the group consisting of —H, $C_1$-$C_4$ alkyl, $C_3$-$C_6$ cycloalkyl, $C_1$-$C_4$ alkanoyl, and $C_1$-$C_4$ enoyl;

$R_3$ is selected from —H, halogen, an optionally halogenated $C_1$-$C_4$ alkyl, $C_1$-$C_4$ alkoxy, or $C_3$-$C_4$ cycloalkyl;

$R_4$ is selected from —O$R_9'$, —CH$_2$N ($R_7'$)($R_8'$);

$R_7'$ and $R_8'$ are each independently selected from —H, an optionally halogenated $C_1$-$C_6$ alkyl, or $C_3$-$C_6$ cycloalkyl; or $R_7'$ and $R_8'$ together with the adjacent N atom form a 5-10 membered heteroaryl ring or a 4-10 membered heterocycle;

$R_9$ is selected from $C_6$-$C_{10}$ aryl, 5-10 membered heteroaryl, or 4-7 membered heterocyclyl;

the $C_6$-$C_{10}$ aryl, 5-6 membered heteroaryl, and 4-6 membered heterocyclyl are each independently and optionally substituted with one or more substituents selected from the group consisting of halogen, $C_1$-$C_4$ alkyl, $C_1$-$C_4$ haloalkyl, and $C_1$-$C_4$ alkoxyl;

the 5-10 membered heteroaryl or heteroaryl ring, and 4-10 membered heterocycle are each independently and optionally substituted with one or more substituents selected from the group consisting of halogen, oxo, $C_1$-$C_6$ alkyl, $C_1$-$C_6$ haloalkyl, and $C_1$-$C_6$ alkoxyl;

each of the 5-6-membered heteroaryl, 4-6 membered heterocyclyl, 5-10 membered heteroaryl or heteroaryl ring, and 4-10 membered heterocycle independently contains 1-3 heteroatoms selected from N, O, and S.

5. The compound, or the deuterated compound, or the pharmaceutically acceptable salt or the prodrug thereof of claim 1, wherein:

M is C or N, and when M is N, $R_2$ is none;

R is amino;

$R_1$ is selected from the group consisting of —H, halogen, hydroxyl, cyano, $C_{1-4}$ alkyl (optionally substituted by halogen, hydroxyl, $C_{1-4}$ alkoxy, trifluoromethoxyl, mono or di $C_{1-4}$ alkylamino), $C_{1-4}$ alkoxy (optionally substituted by halogen, hydroxyl, $C_{1-4}$ alkoxyl, amino, mono or di $C_{1-4}$ alkylamino), amino, mono or di $C_{1-4}$ alkylamino, $C_{1-4}$ alkylamido, $C_{3-6}$ cycloalkylamido, and $C_{2-4}$ alkenylamido optionally substituted by mono or di $C_{1-4}$ alkylamino;

$R_2$ is selected from —H, or halogen;

$R_3$ is selected from the group consisting of —H, halogen, cyano, an optionally halogenated $C_{1-4}$ alkyl, $C_{1-4}$ alkoxy;

R4 is a C1-4 alkyl or oxyl substituted by a 5- or 6-membered aliphatic heterocyclyl having 1-2 N atoms on the ring, wherein the 5- or 6-membered aliphatic heterocyclyl is optionally substituted by C1-4 alkyl.

6. The compound, or the deuterated compound, or the pharmaceutically acceptable salt or the prodrug thereof of claim 1, wherein the compound, or the deuterated compound, or the pharmaceutically acceptable salt or the prodrug thereof is selected from the following compounds:

HuFGFR267

HuFGFR302

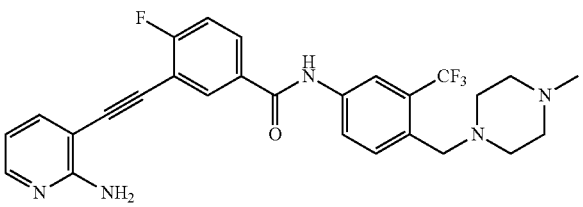

HuFGFR301

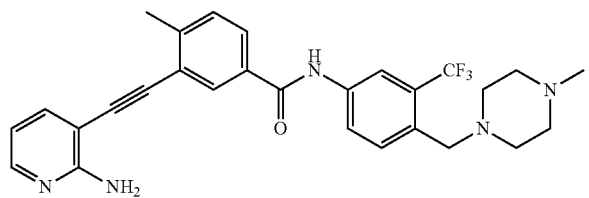

HuFGFR321

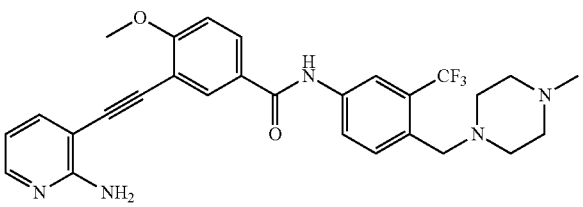

HuFGFR322

HuFGFR293

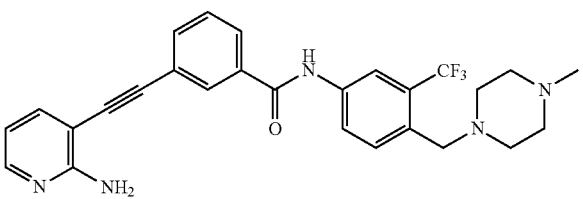

HuFGFR315
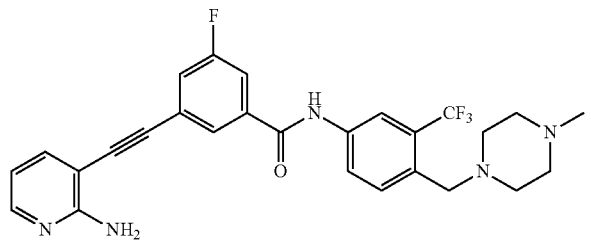
HuFGFR314
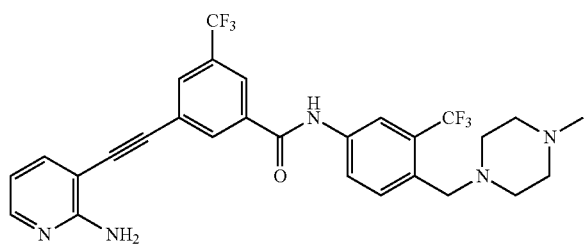
HuFGFR327
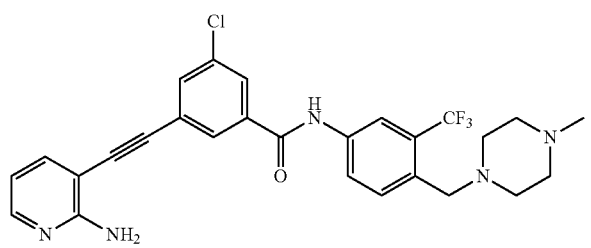
HuFGFR329
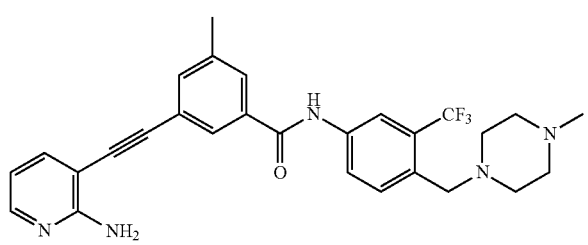
HuFGFR330
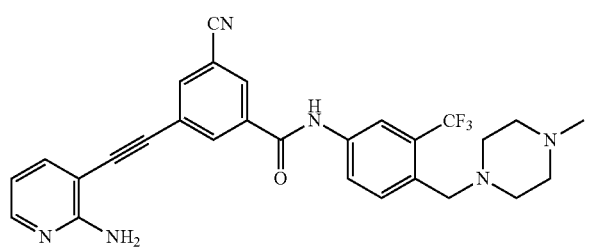
HuFGFR331
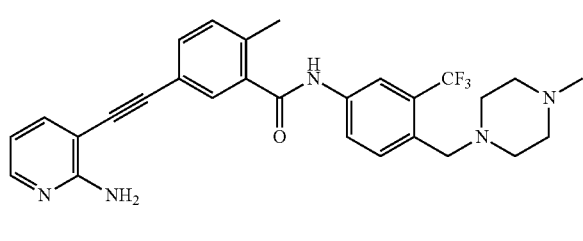
HuFGFR332
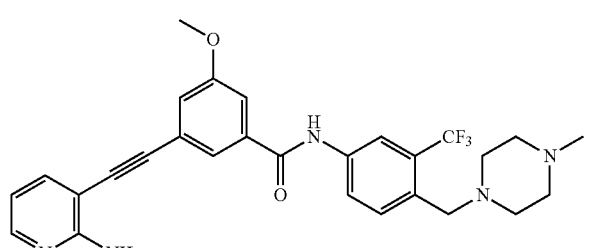
HuFGFR333
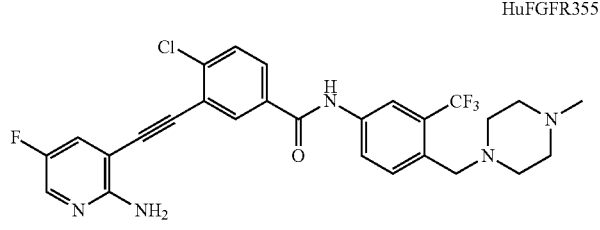
HuFGFR334
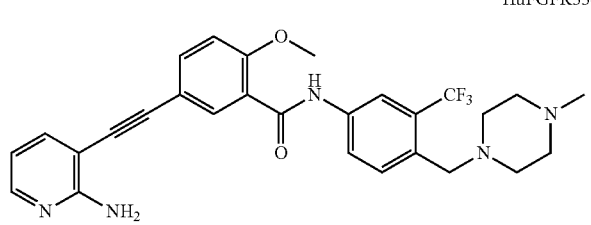
HuFGFR355
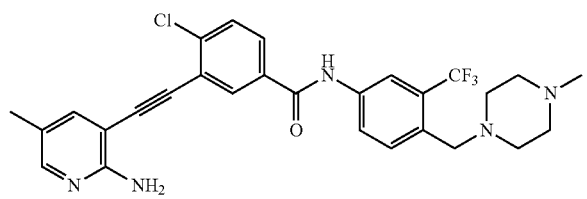
HuFGFR356
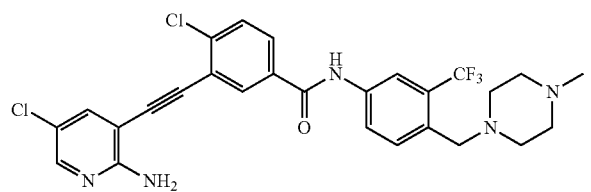
HuFGFR357

-continued
HuFGFR358
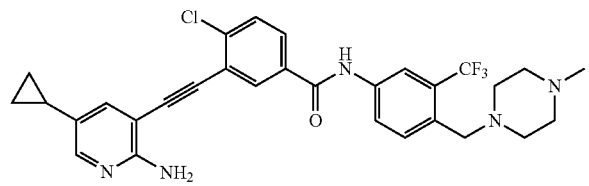
HuFGFR307
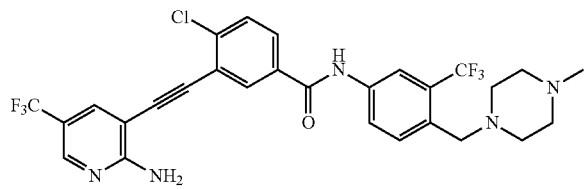
HuFGFR359
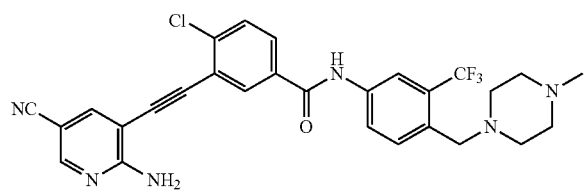
HuFGFR360
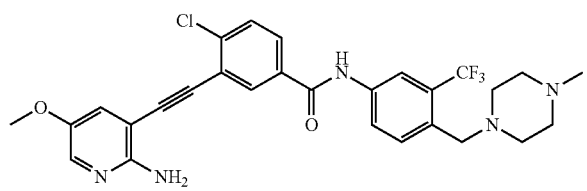
HuFGFR361
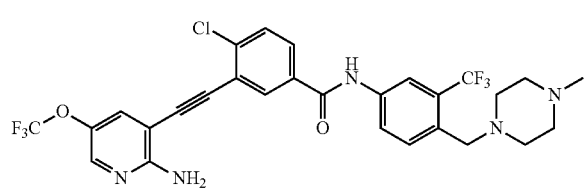
HuFGFR362
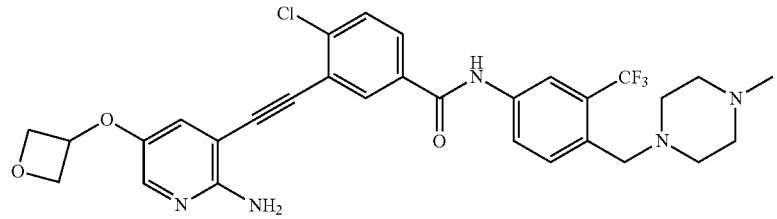
HuFGFR363
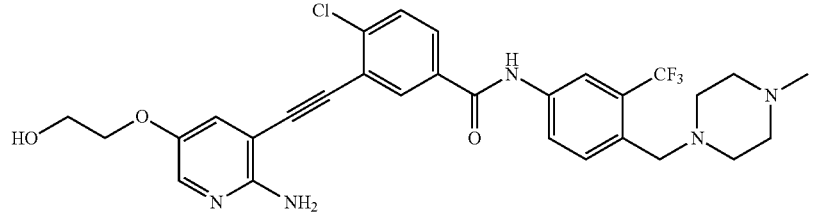
HuFGFR377
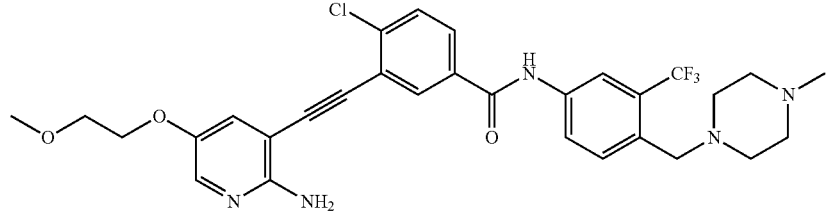
HuFGFR378
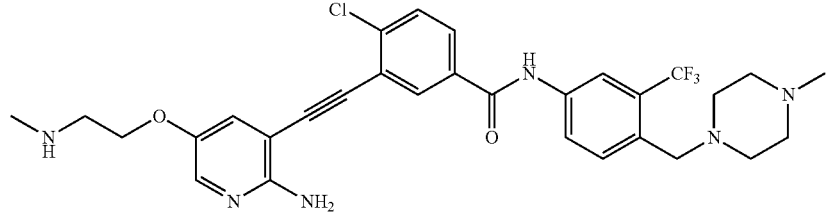
HuFGFR379

-continued
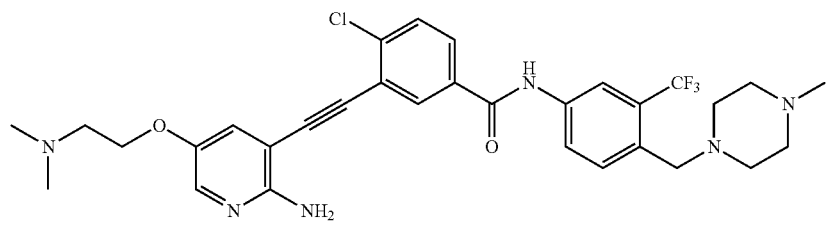
HuFGFR380
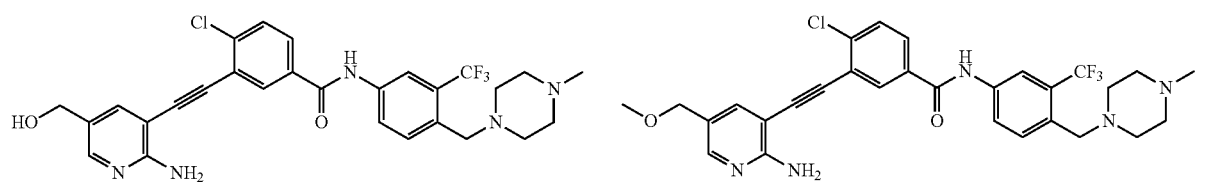
HuFGFR384          HuFGFR385
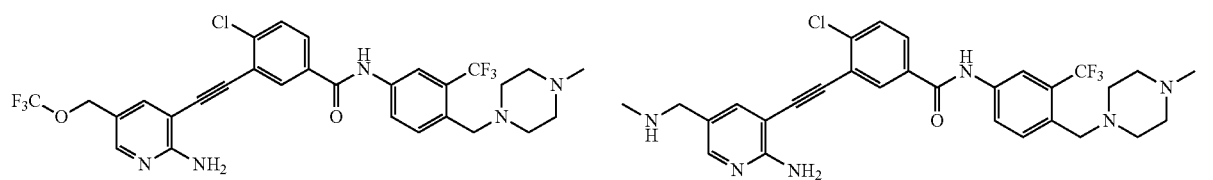
HuFGFR386          HuFGFR387
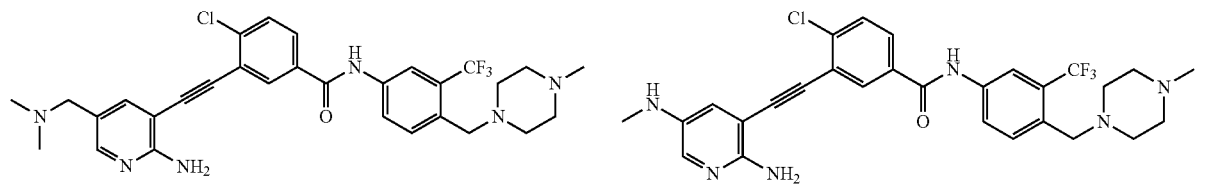
HuFGFR388          HuFGFR389
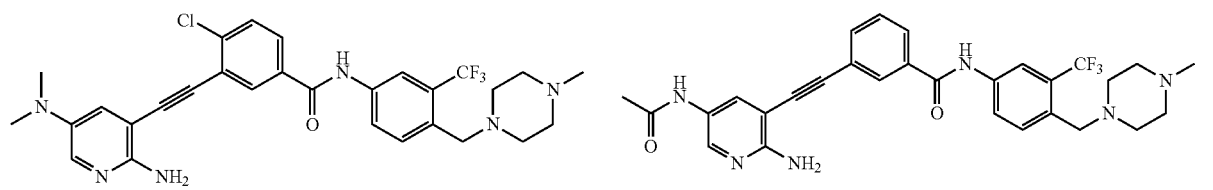
HuFGFR390          HuFGFR392
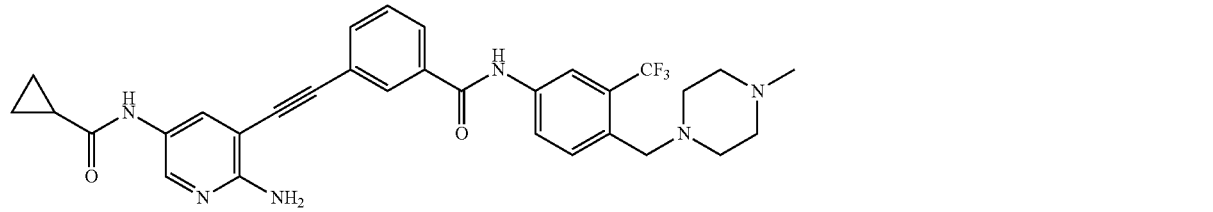
HuFGFR396
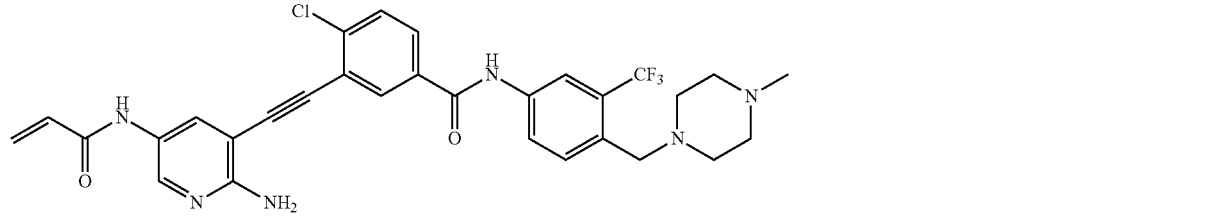
HuFGFR284

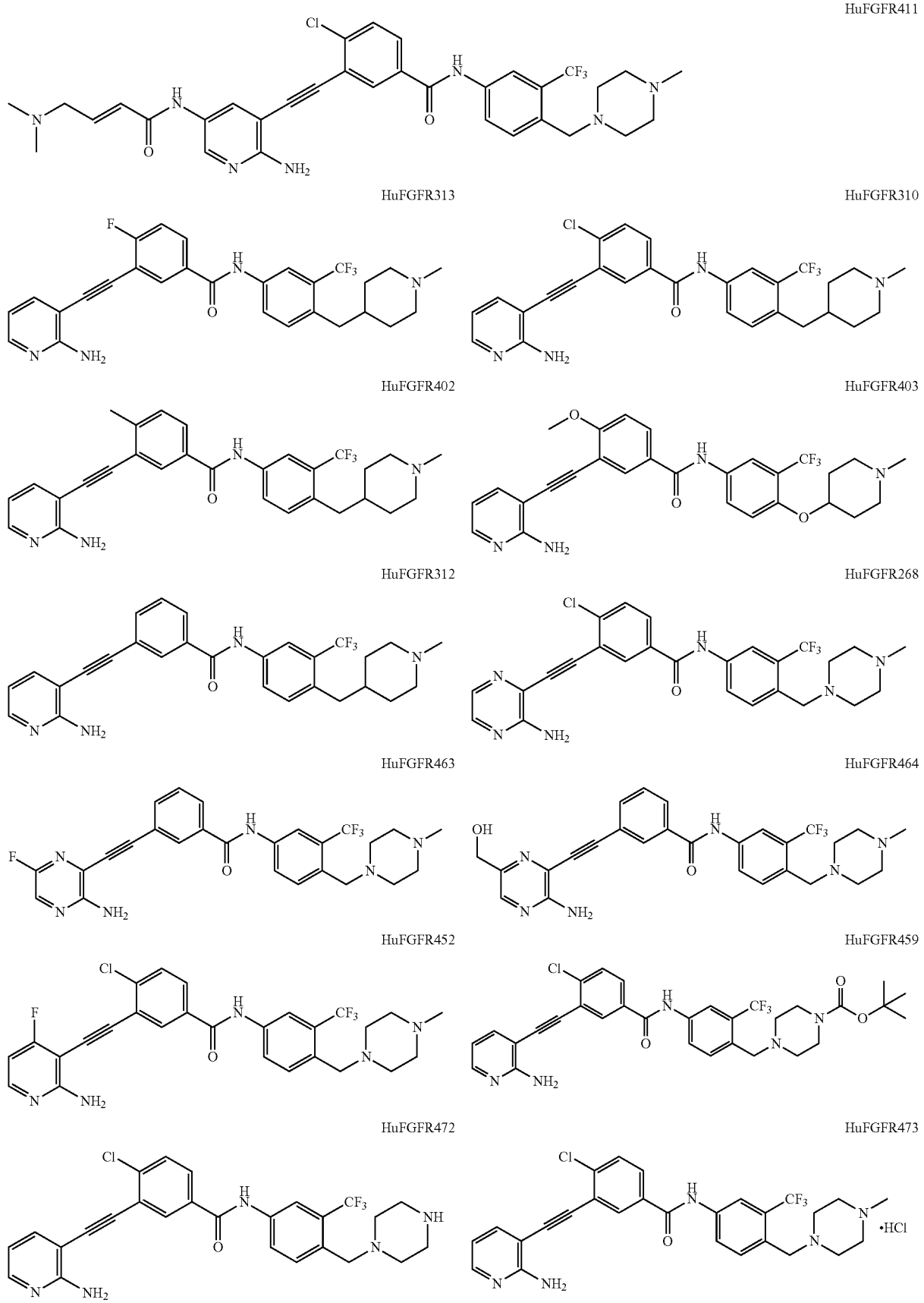

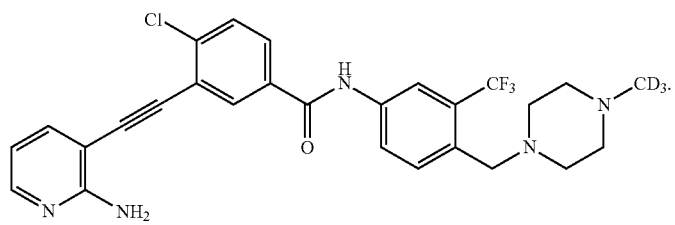

HuFGFR474

7. A method for preparing the compound of formula (I), or the deuterated compound, or the pharmaceutically acceptable salt or the prodrug thereof of claim 1, which comprises a step of reacting a compound of formula (1) with a compound of formula (2)

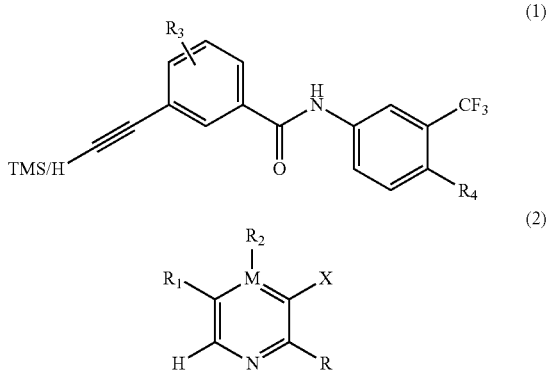

wherein, each of R and $R_1$-$R_4$ is independently defined as claim 1.

8. A pharmaceutical composition, which comprises the compound of formula (I), the deuterated compound, or the pharmaceutically acceptable salt or the prodrug thereof of claim 1, and a pharmaceutically acceptable excipient.

9. The compound, or the deuterated compound, or the pharmaceutically acceptable salt or the prodrug thereof of claim 1, wherein the pharmaceutically acceptable salt comprises hydrochloride, methanesulfonate, or maleate of the compound of formula (I), and the prodrug comprises ester, amide, or carboxamide of the compound of formula (I).

10. A method for treating tumor in a subject, which comprises a step of administering a safe and effective amount of a compound of formula (I), or a deuterated compound, or a pharmaceutically acceptable salt or a prodrug thereof of claim 1 to a subject in need;
wherein the tumor is selected from the group consisting of non-small cell lung cancer, breast cancer, thyroid cancer, gastric cancer, bladder cancer, endometrial cancer, prostate cancer, cervical cancer, colon cancer, esophageal cancer, keratinoma, myeloma, rhabdomyosarcoma, acute leukemia, liver cancer, adenocarcinoma, and pancreatic cancer.

11. The method of claim 10, wherein the thyroid cancer comprises medullary thyroid carcinoma and papillary thyroid cancer.

12. The method of claim 7 which comprises:
in the presence of a transition metal palladium and copper catalyst and in alkaline condition, coupling the compound of formula (1) with the compound of formula (2).

13. The method of claim 7, wherein the palladium catalyst comprises $Pd(PPh_3)_2Cl_2$, $Pd(OAc)_2$, and/or $Pd(PPh_3)_4$;
the copper catalyst comprises CuI and/or CuCl;
the base used for the alkaline condition comprises one or more bases selected from CsF, $Cs_2CO_3$, $K_2CO_3$, triethylamine, diisopropylethylamine, and DMAP; and/or
the solvent for coupling reaction comprises one or more solvents selected from acetonitrile, 1,4-dioxane, and DMF.

14. The method of claim 7, which comprises a step of reacting the compound of formula (1) with the compound of formula (2) in the presence of cesium fluoride, $Pd(PPh_3)_2Cl_2$, CuI and triethylamine and in acetonitrile as a solvent.

15. The compound, or the deuterated compound, or the pharmaceutically acceptable salt or the prodrug thereof of claim 2, wherein:
the alkyl is methyl, ethyl, propyl, isopropyl or tert-butyl;
the aryl is a 6-8 membered monocyclic or fused bicyclic ring;
the heteroaryl or heteroaryl ring is a 6-8 membered monocyclic or fused bicyclic ring containing 1-3 heteroatoms selected from N, O and S; and
the heterocyclyl is a 4-6 membered monocyclic or polycyclic heterocycle containing 1-3 heteroatoms selected from N, O, and S.

16. The compound, or the deuterated compound, or the pharmaceutically acceptable salt or the prodrug thereof of claim 3, wherein:
the $C_6$-$C_{10}$ aryl is optionally substituted with 1-5 substituents selected from the group consisting of halogen, $C_1$-$C_6$ alkyl, $C_1$-$C_6$ haloalkyl, and $C_1$-$C_6$ alkoxyl.

17. The compound, or the deuterated compound, or the pharmaceutically acceptable salt or the prodrug thereof of claim 5, wherein:
$R_3$ is hydrogen, chloro, fluoro, methyl, methoxyl, cyano, or trifluoromethyl; and
$R_4$ is 4-methylpiperazin-1-ylmethyl or 1-methylpiperidin-4-yloxyl.

* * * * *